(12) United States Patent
Satoh et al.

(10) Patent No.: US 7,635,704 B2
(45) Date of Patent: Dec. 22, 2009

(54) STABLE CRYSTAL OF 4-OXOQUINOLINE COMPOUND

(75) Inventors: Motohide Satoh, Osaka (JP); Takahisa Motomura, Osaka (JP); Takashi Matsuda, Osaka (JP); Kentaro Kondo, Osaka (JP); Koji Ando, Osaka (JP); Koji Matsuda, Osaka (JP); Shuji Miyake, Osaka (JP); Hideto Uehara, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 488 days.

(21) Appl. No.: 11/133,471

(22) Filed: May 20, 2005

(65) Prior Publication Data

US 2006/0030710 A1  Feb. 9, 2006

(30) Foreign Application Priority Data

May 20, 2004  (JP) ............................. 2004-150979

(51) Int. Cl.
 A61K 31/4704 (2006.01)
 C07D 215/36 (2006.01)
(52) U.S. Cl. .................. 514/312; 514/300; 546/123; 546/156
(58) Field of Classification Search .............. 514/300, 514/312; 546/123, 156
 See application file for complete search history.

(56) References Cited

U.S. PATENT DOCUMENTS

| 3,472,859 | A | 10/1969 | Lesher |
| 5,519,016 | A | 5/1996 | Kimura et al. |
| 5,688,791 | A | 11/1997 | Kimura et al. |
| 5,985,894 | A | 11/1999 | Clemence et al. |
| 6,034,086 | A | 3/2000 | Kimura et al. |
| 6,248,736 | B1 | 6/2001 | Turner et al. |
| 6,248,738 | B1 | 6/2001 | Dickinson et al. |
| 6,248,739 | B1 | 6/2001 | Turner et al. |
| 6,559,145 | B2 | 5/2003 | Ciske et al. |
| 6,627,646 | B2 * | 9/2003 | Bakale et al. ............... 514/322 |
| 6,670,377 | B1 | 12/2003 | Mekouar et al. |
| 2002/0103220 | A1 | 8/2002 | Schnute |
| 2003/0138483 | A1 * | 7/2003 | Petriconi et al. ............. 424/456 |
| 2004/0127708 | A1 | 7/2004 | Fuji et al. |
| 2005/0239819 | A1 | 10/2005 | Satoh et al. |
| 2005/0288326 | A1 | 12/2005 | Matsuzaki et al. |
| 2006/0019906 | A1 * | 1/2006 | Satoh et al. .................... 514/23 |

FOREIGN PATENT DOCUMENTS

| EP | 498721 | B1 | 8/1992 |
| EP | 1140851 | B1 | 10/2001 |
| EP | 1375486 | A1 | 1/2004 |
| EP | 1 564 210 | A1 | 8/2005 |
| JP | A 48 26 772 | | 4/1973 |
| JP | A 43 60 872 | | 12/1992 |
| JP | 6-116241 | A | 4/1994 |
| JP | 6-199835 | A | 7/1994 |
| JP | 6-271568 | A | 9/1994 |
| JP | 8-183775 | A | 7/1996 |
| JP | 10-316570 | A | 12/1998 |
| JP | 2002-293745 | | 10/2002 |
| JP | A 2002-534416 | | 10/2002 |
| JP | A 2002-534417 | | 10/2002 |
| JP | 3567162 | | 9/2004 |
| WO | WO 97/38999 | | 10/1997 |
| WO | WO 98/45269 | | 10/1998 |
| WO | WO 00/01714 | | 1/2000 |
| WO | WO 00/40561 | | 7/2000 |
| WO | WO 00/40563 | | 7/2000 |
| WO | WO 01/98275 | A2 | 12/2001 |
| WO | WO 02/04444 | | 1/2002 |
| WO | WO 02/36734 | A2 | 5/2002 |
| WO | WO 02/055079 | A2 | 7/2002 |
| WO | WO 02/070486 | A1 | 9/2002 |
| WO | WO 03/010147 | A1 | 2/2003 |

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al. "Physicochemical behavior or active . . . " CA 132:325872 (2000).*
Otsuka et al. "effect of polymorphic . . . " Chem. Pharm. Bull, 47(6) 852-856 (1999).*
Brittain "Polymorphism in pharmaceutical solids" Marcel Dekker inc. p. 2, (1999).*
US Pharmacopia #23 national formulary #18, p. 1843-1844 (1995).*
Wikipedia "Polymorphosm" free encyclopedia (2006).*
Engleson "Concise encyclopedia Chemistry" p. 872-873 (1993).*
Sleasman et al. "HIV-1 infection" CA 139:305926 (2003).*
Parienti "Cytokine therapy or structured treatment . . . " CA 137:92237 (2002).*
Goho "Tricky business" Science News online, (Aug. 2004) p. 1-9.*
Knapman "polymorph prediction" The Alchemist (Oct. 1999) 1/2, p. 1-3, 2/2, p. 1-3.*
Brittain "polymorphism . . . " p. 57-58 (1999).*
Bernstein "Polymorphism . . . " p. 108 (2002).*

(Continued)

*Primary Examiner*—Celia Chang
(74) *Attorney, Agent, or Firm*—Finnegan, Henderson, Farabow, Garrett & Dunner, LLP

(57) ABSTRACT

Provision of a stabilized crystal of 6-(3-chloro-2-fluorobenzyl)-1-[(S)-1-hydroxymethyl-2-methylpropyl]-7-methoxy-4-oxo-1, 4-dihydroquinoline-3-carboxylic acid (compound A). A crystal of compound A, which shows a particular X-ray powder diffraction pattern of a characteristic diffraction peaks at diffraction angles 2θ(°) as measured by X-ray powder diffractmetry.

15 Claims, 2 Drawing Sheets

OTHER PUBLICATIONS

Ulrich Crystallization{ Kirk-Othmer encyclopedia of chem. tech. p. 95-147 (2002).*
CMU Pharmaceutical polymorphism, internat p. 1-3 (2002) (print out Apr. 3, 2008).*
Singhal et al. "Drug polymorphism . . . " Advanced drug delivery reviews 56. p. 335-347 (2004).*
Lanz et al. "Pharmaceutical powder technology . . . " (2006) p. 110.*
Marsac et al. "Sppontaneous crystallinity loss . . . " J. Pharm Sci. v. 97(8) p. 3182-3194 (2008).*
Elbary et al. "Polymorphic transformation . . . " CA 136:58666 (2001).*
Nair et al. "Influence of polyethylene glycol and povidone . . . " CA 138:260244 (2002).*
Henck et al. "Designing a molecular . . . " Drug. disclovery Today v. 12(5/6) p. 189-199 (2007).*
Niazi "handbook of pharmaceutical manufacturing . . . " p. 1( form internet ) (2004).*
Cushman et al. "Cosalane analogues . . . " J. Med. Chem. v.38, p. 443-52 (1995).*
Abdul-Ahad, *Europ. J. of Med. Chem*, 17(4), pp. 301-306 (1982).
Baker, *J. Med. Chem*, 15(3), pp. 235-237 (1972).
Chou and Talalay, Adv. Enzyme Regul. 22:27-55 (1984).
*Guidelines for the Use of Antiretroviral Agents in HIV-Infected Adults and Adolescent*, pp. i-iii and 1-111, (Aug. 13, 2001).
Hirao, I. et al., *Studies on the Synthesis of Quinoline Compounds, I.* Memoirs Kyushu Inst. Tech. (Eng.), 14:13-16 (1984).
Hirao, I. et al., *Antibacterial Activities of Oxodihydroquinoline Carboxylic Acid Derivatives*, Memoirs Department of Engineering, 14:21-32 (1990).
Mol. Pharmacol. 10:235-247 (1974).
Stefancich, Farmaco, Edizioje Scientific, 42(1), pp. 3-16 (1987).
Vincent, K.A., et al., *Characterization of Human Immunodeficiency Virus Type I Integrase Expressed In Eschericia coli and Analysis of Variants with Amino-Terminal Mutations*, J. Virol. 67: 425-437 (1993).
Walton, *Antimicrobial Agents*, Chemotherapy, 32(7) pp. 10869 (1988).
Yoshimoto, *J. Med. Chem*, 19(1), pp. 71-98 (1976).
PCT International Search Report (PCT/JP2005/009604) dated Nov. Oct. 28, 2005.

* cited by examiner

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination of
      HIV integrase.

<400> SEQUENCE: 1 accctttag tcagtgtgga aaatctctag ca                                      32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination
      of HIV integrase.

<400> SEQUENCE: 2
actgctagag attttccaca ctgactaaaa g                                      31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase.

<400> SEQUENCE: 3
tgaccaaggg ctaattcact                                                   20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination
      of HIV integrase.

<400> SEQUENCE: 4
agtgaattag cccttggtca                                                   20

STABLE CRYSTAL OF 4-OXOQUINOLINE COMPOUND

CROSS-REFERENCE TO RELATED APPLICATIONS

This application claims the benefit of priority under 35 U.S.C. § 119 (a) to JP 2004-150979 filed May 20, 2004, which is incorporated herein by reference.

TECHNICAL FIELD

The present invention relates to a stable crystal of 6-(3-chloro-2-fluorobenzyl)-1-[(S)-1-hydroxymethyl-2-methylpropyl]-7-methoxy-4-oxo-1,4-dihydroquinoline-3-carboxylic acid

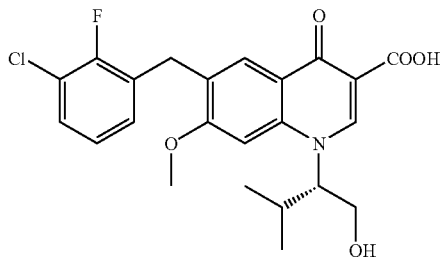

(hereinafter sometimes to be compound A) and a mixed crystal thereof. The present invention also relates to a pharmaceutical composition comprising the crystal or the mixed crystal.

BACKGROUND ART

The present Applicant has disclosed in a Japanese Patent filed by the same Applicant that the above-mentioned compound A has an inhibitory action on integrase that is an essential enzyme for the growth of HIV (Human Immunodeficiency Virus), which is a causative virus of AIDS (Acquired Immunodeficiency Syndrome), and shows an anti-HIV effect (particularly Example 4-32 and Experimental Example).

In general, when a compound is used as a pharmaceutical product, chemical and physical stability of the compound is required so as to maintain quality and/or facilitate preservation. Not only the final pharmaceutical composition but also a compound as a synthetic starting material is desirably chemically and physically stable for the same reasons.

Therefore, such compound is preferably a crystal, particularly preferably a stable crystal. When the compound has crystal polymorphism, the most stable crystal is generally selected.

While the above-mentioned patent describes compound A, no concrete description relating to the crystal form of compound A is found.

SUMMARY OF THE INVENTION

Thus, the present inventors have studied various crystal forms of compound A in an attempt to find a stable crystal of compound A. As a result, they have found that compound A has crystal polymorphism, and a crystal of compound A having a particular crystal form is useful as a stable crystal, and based on which findings, they have completed the present invention.

Accordingly, one or more embodiments of the present invention provide the following.

[1] A crystal (crystal form II) of 6-(3-chloro-2-fluorobenzyl)-1-[(S)-1-hydroxymethyl-2-methylpropyl]-7-methoxy-4-oxo-1,4-dihydroquinoline-3-carboxylic acid, which has an X-ray powder diffraction pattern having characteristic diffraction peaks at diffraction angles 2θ(°) of 6.56, 13.20, 19.86, 20.84, 21.22, 25.22° as measured by X-ray powder diffractometer;

[2] a crystal (crystal form III) of 6-(3-chloro-2-fluorobenzyl)-1-[(S)-1-hydroxymethyl-2-methylpropyl]-7-methoxy-4-oxo-1,4-dihydroquinoline-3-carboxylic acid, which has an X-ray powder diffraction pattern having characteristic diffraction peaks at diffraction angles 2θ(°) of 8.54, 14.02, 15.68, 17.06, 17.24, 24.16, 25.74° as measured by X-ray powder diffractometer;

[3] a crystal (crystal form III) of 6-(3-chloro-2-fluorobenzyl)-1-[(S)-1-hydroxymethyl-2-methylpropyl]-7-methoxy-4-oxo-1,4-dihydroquinoline-3-carboxylic acid, having an extrapolated onset temperature of 162.1±5.0° C.;

[4] the crystal of any of the above-mentioned [1] to [3], which has a purity of crystal of not less than 70%;

[5] a mixed crystal comprising the crystal of the above-mentioned 1 and the crystal of the above-mentioned [2] or [3];

[6] the mixed crystal of the above-mentioned [5], wherein the purity of crystal is not less than 70%;

[7] a pharmaceutical composition comprising the crystal of any of the above-mentioned [1] to [4] or the mixed crystal of the above-mentioned [5] or [6], and a pharmaceutically acceptable carrier;

[8] an integrase inhibitor comprising the crystal of any of the above-mentioned [1] to [4] or the mixed crystal of the above-mentioned [5] or [6] as an active ingredient;

[9] an antivirus agent comprising the crystal of any of the above-mentioned [1] to [4] or the mixed crystal of the above-mentioned [5] or [6] as an active ingredient;

[10] an anti-HIV agent comprising the crystal of any of the above-mentioned [1] to [4] or the mixed crystal of the above-mentioned [5] or [6] as an active ingredient;

[11] an anti-HIV composition comprising the crystal of any of the above-mentioned [1] to [4] or the mixed crystal of the above-mentioned [5] or [6] and one or more kinds of other anti-HIV active substances as active ingredients; and

[12] an anti-HIV agent for a multiple drug therapy with other anti-HIV agent, which comprises the crystal of any of the above-mentioned [1] to [4] or the mixed crystal of the above-mentioned [5] or [6] as an active ingredient.

The crystal or mixed crystal of compound A of the present invention has the above-mentioned particular crystal form and is superior in physical and chemical stability, which in turn has advantage that maintenance of the quality of compound A for a long-term becomes possible, which facilitates preservation. In addition, they have advantage that handling during production of various pharmaceutical compositions and bulk is easy, which reduces the production cost.

DETAILED DESCRIPTION OF THE INVENTION

The present invention is explained in detail in the following.

The term "crystal form II" of compound A means a crystal of compound A, which has an X-ray powder diffraction pattern having characteristic diffraction peaks at diffraction angles 2θ(°) of 6.56, 13.20, 19.86, 20.84, 21.22, 25.22° as measured by X-ray powder diffractometer.

The term "crystal form III" of compound A means a crystal of compound A, which has an X-ray powder diffraction pattern having characteristic diffraction peaks at diffraction angles 2θ(°) of 8.54, 14.02, 15.68, 17.06, 17.24, 24.16, 25.74° as measured by X-ray powder diffractometer.

The diffraction peak value at the above-mentioned diffraction angle 2θ(°) may show slight measurement error due to the measurement instruments or measurement conditions and the like. To be specific, the measurement error may be within the range of about ±0.2, preferably about ±0.1, more preferably about ±0.06.

In an embodiment, crystal of compound A of the present invention is also characterized by thermal analysis. For example, when the crystal form III of compound A of the present invention is subjected to Differential Scanning Calorimetry (DSC), the enthalpy of endothermic peak is about 81 J/g, and extrapolated onset temperature is 162.1±5.0° C., preferably 162.1±3.0° C., more preferably 162.1±1.0° C., wherein the "extrapolated onset temperature" means, as defined by JIS K 7121 (measurement method of transfer temperature of plastic), the temperature at an intersection of the extrapolated baseline of the lower temperature side toward the higher temperature side with the tangent line drawn at the point showing the greatest slope on the leading edge of the melting peak on a lower temperature side in a DSC curve. When the enthalpy and extrapolated onset temperature of the endothermic peak is within the above-mentioned range, the crystal of compound A is stable.

In an embodiment, the crystal of compound A of the present invention may be either a crystal form II or a crystal form III, or a mixed crystal of a crystal form II and a crystal form III. For use in a pharmaceutical product of compound A and the like, the crystal form II or crystal form III is preferable because they are stable crystals, and a crystal form III is more preferable because it is the most stable crystal. In addition, a crystal form II is preferable in view of the absorbability by living organisms upon administration as a pharmaceutical composition.

The term "purity of crystal" means the purity of the crystal form II or crystal form III of compound A. In the case of a mixed crystal of a crystal form II and a crystal form III, it means the ratio of crystal relative to the total amount of substance of a crystal form II and a crystal form III. The purity of the crystal of the present invention can be determined by, for example, known methods such as X-ray powder diffractometry, thermal analysis, and the like. The purity of the crystal or mixed crystal of the present invention does not need to be 100%, and may be not less than 70%, preferably not less than 80%, more preferably not less than 90%, more preferably not less than 95%, more preferably not less than 98% Purity within this range is preferable for guaranteeing the quality.

The crystal or mixed crystal of compound A of the present invention can be administered to a mammal (human, mouse, rat, hamster, rabbit, cat, dog, bovine, sheep, monkey, and the like.), and the like as various pharmaceutical compositions such as anti-HIV agents, HIV integrase inhibitors, antivirus agents, and the like used for, for example, the prophylaxis and/or treatment of AIDS.

When the crystal or mixed crystal of compound A of the present invention is used as a pharmaceutical composition, it is admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, and other additives, that are generally known, such as water, vegetable oil, alcohol (e.g., ethanol or benzyl alcohol, or the like.), polyethylene glycol, glycerol triacetate, gelatin, carbohydrate (e.g., lactose, starch, and the like.), magnesium stearate, talc, lanolin, petrolatum, and the like, formed into tablet, pill, powder, granule, suppository, injection, eye drop, liquid, capsule, troche, aerosol, elixir, suspension, emulsion, syrup, and the like by a conventional method, and administered systemically or topically, and orally or parenterally.

While the dose varies depending on age, body weight, symptom, treatment effect, administration method, and the like, it is generally from about 0.01 mg to about 1 g per administration for an adult, which is given once to several times a day orally or in a dosage form of an injection such as intravenous injection and the like.

An anti-HIV agent is generally required to sustain its effect for a long time, so that it can be effective not only for temporal suppression of viral growth but also for the prohibition of viral re-growth. This means that a prolonged administration is necessary and that a high single dose may be frequently inevitable to sustain the effect for a longer period during night and the like. Such prolonged and high dose administration increases the risk of side effects.

In view of this, one of the preferable modes of the present invention is such compound permitting high absorption by oral administration, and such compound capable of maintaining blood concentration of the administered compound for an extended period of time.

By the "prophylaxis of AIDS" is meant, for example, administration of a pharmaceutical agent to an individual who tested HIV positive but has not yet developed the disease state of AIDS, administration of a pharmaceutical agent to an individual who shows an improved disease state of AIDS after treatment but who carries HIV still to be eradicated and whose relapse of AIDS is worried, and administration of a pharmaceutical agent out of a fear of possible infection.

The anti-HIV composition of the present invention is used for, for example, a multiple drug combination therapy of AIDS. Examples of the "other anti-HIV active substance" to be used for the anti-HIV composition include an anti-HIV antibody, an HIV vaccine, immunostimulants such as interferon, and the like, an HIV ribozyme, an HIV antisense drug, an HIV reverse transcriptase inhibitor, an HIV protease inhibitor, an inhibitor of bond between a bond receptor (CD4, CXCR4, CCR5, and the like) of a host cell recognized by virus and the virus, and the like.

Specific examples of the HIV reverse transcriptase inhibitor include Retrovir® (zidovudine), Epivir® (lamivudine), Zerit® (sanilvudine), Videx® (didanosine), Hivid® (zalcitabine), Ziagen® (abacavir sulfate), Viramune® (nevirapine), Stocrin® (efavirenz), Rescriptor® (delavirdine mesylate), Combivir® (zidovudine+lamivudine), Trizivir® (abacavir sulfate+lamivudine+zidovudine), Coactinon® (emivirine), Phosphonovir®, Coviracil®, alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis(isopropoxycarbonyloxymethyl)ester fumarate), DPC-083 ((4S)-6-chloro-4-[(1E)-cyclopropylethenyl]-3,4-dihydro-4-trifluoromethyl-2 (1H)-quinazolinone), DPC-961 ((4S)-6-chloro-4-(cyclopropylethynyl)-3,4-dihydro-4-(trifluoromethyl)-2 (1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, UC-781, BCH-10618, DPC-083, Etravirine, BCH-13520, MIV-210, Abacavir sulfate/lamivudine, GS-7340, GW-5634, GW-695634, and the like, wherein (R) means a registered trademark (hereinafter the same) and the names of other pharmaceutical agents are general names.

Specific examples of the HIV protease inhibitor include Crixivan® (indinavir sulfate ethanolate), saquinavir, Invirase® (saquinavir mesylate), Norvir® (ritonavir), Viracept® (nelfinavir mesylate), lopinavir, Prozei® (amprenavir), Kaletra® (ritonavir+lopinavir), mozenavir dimesylate ([4R-(4α,5α,6β)]-1,3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5 (S)-(tert-butoxycarbonylamino)-4 (S)-hydroxy-6-phenyl-2 (R)-(2,3,4-trimethoxybenzyl)hexanoyl]-L-valine 2-methoxyethylenamide), KNI-272 ((R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2 (R)-hydroxy-1(S)-indanyl)-2 (R)-phenylmethyl-4 (S)-hydroxy-5-[4-(2-benzo[b]furanylmethyl)-2 (S)-(tert-butylcarbamoyl)piperazin-1-yl]pentanamide)+indinavir sulfate), JE-2147 ([2 (S)-oxo-4-phenylmethyl-3 (S)-[(2-methyl-3-oxy)phenylcarbonylamino]-1-oxabutyl]-4-[(2-methylphenyl)methylamino]carbonyl-4 (R)-5,5-dimethyl-1,3-thiazole), BMS-232632 ((3S,8S,9S,12S)-3,12-bis(1,1-dimethylethyl)-8-hydroxy-4,11-dioxo-9-(phenylmethyl)-6-[[4-(2pyridinyl)phenyl]methyl]-2,5,6,10,13-pentaazatetradecanedicarboxylic acid dimethyl ester), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649, AG-1859, and the like.

The HIV integrase inhibitor is exemplified by S-1360, L-870810, and the like, the DNA polymerase inhibitor or DNA synthesis inhibitor is exemplified by Foscavir®, ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4 propyl-2H,6H,10H-benzo[1,2-b:3,4-b':5,6-b"]tripyran-2-one), calanolide B, NSC-674447 (1,1'-azobisformamide), Iscador (viscum alubm extract), Rubitecan, and the like, the HIV antisense drug is exemplified by HGTV-43, GEM-92, and the like, the anti-HIV antibody or other antibody is exemplified by NM-01, PRO-367, KD-247, Cytolin®, TNX-355 (CD4 antibody), AGT-1, PRO-140 (CCR5 antibody), Anti-CTLA-4Mab, and the like, the HIV vaccine or other vaccine is exemplified by ALVAC®, AIDSVAX®, Remune®, HIVgp41 vaccine, HIVgp120 vaccine, HIVgp140 vaccine, HIVgp160 vaccine, HIVp17 vaccine, HIVp24 vaccine, HIVp55 vaccine, AlphaVax Vector System, canarypox gp160 vaccine, AntiTat, MVA-F6 Nef vaccine, HIVrev vaccine, C4-V3 peptide, p2249f, VIR-201, HGP-30W, TBC-3B, PARTICLE-3B, and the like, Antiferon (interferon-α vaccine), and the like, the interferon or interferon agonist is exemplified by Sumiferon®, MultiFeron®, interferon-τ, Reticulose, human leukocyte interferon α, and the like, the CCR5 antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl] naphthyl-2,5-dimethoxyphenyl-1,4-dihydrazone), T-1249, Synthetic Polymeric Construction No3, pentafuside, FP-21399, PRO-542, Enfuvirtide, and the like, the IL-2 agonist or antagonist is exemplified by interleukin-2, Imunace®, Proleukin®, Multikine®, Ontak®, and the like, the TNF-α antagonist is exemplified by Thalomid® (thalidomide), Remicade® (infliximab), curdlan sulfate, the α-glucosidase inhibitor is exemplified by Bucast® and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z®, Panavir®, Coenzyme Q10 (2-deca(3-methyl-2-butenylene)-5,6-dimethoxy-3-methyl-p-benzoquinone), and the like, the cholinesterase inhibitor is exemplified by Cognex® and the like, and the immunomodulator is exemplified by Imunox®, Prokine®, Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602, and the like.

In addition, Neurotropin®, Lidakol®, Ancer 20®, Ampligen®, Anticort®, Inactivin®, and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)-FTC, Ushercell, D2S, BufferGel®, VivaGel®, Glyminox vaginal gel, sodium lauryl sulfate, 2F5, 2F5/2G12, VRX-496, Ad5gag2, BG-777, IGIV-C, BILR-255, and the like are exemplified.

As the "other anti-HIV activity substance" to be used for the anti-HIV composition of the present invention in the multiple drug combination therapy, preferred are an HIV reverse transcriptase inhibitor and an HIV protease inhibitor. Two or three, or even a greater number of pharmaceutical agents can be used in combination, wherein a combination of pharmaceutical is agents having different action mechanisms is one of the preferable embodiments. In addition, selection of pharmaceutical agents free of side effect duplication is preferable.

Specific examples of the combination of pharmaceutical agents include a combination of a group consisting of efavirenz, tenofovir, emtricitabine, indinavir, nelfinavir, atazanavir, ritonavir+indinavir, ritonavir+lopinavir and ritonavir+saquinavir, didanosine+lamivudine, zidovudine+didanosine, stavudine+didanosine, zidovudine+lamivudine, stavudine+lamivudine and emtriva, and the crystal or mixed crystal of the present invention (Guidelines for the Use of Antiretroviral Agents in HIV-Infected Adults and Adolescents. Aug. 13, 2001). Particularly preferred is a combined use of two agents of the crystal or mixed crystal of the present invention with efavirenz, indinavir, nelfinavir, tenofovir, emtricitabine, zidovudine or lamivudine, and a combined use of three agents of the crystal or mixed crystal of the present invention with zidovudine+lamivudine, tenofovir+lamivudine, tenofovir+zidovudine, tenofovir+efavirenz, tenofovir+nelfinavir, tenofovir+indinavir, tenofovir+emtricitabine, emtricitabine+lamivudine, emtricitabine+zidovudine, emtricitabine+efavirenz, emtricitabine+nelfinavir, emtricitabine+indinavir, nelfinavir+lamivudine, nelfinavir+zidovudine, nelfinavir+efavirenz, nelfinavir+indinavir, efavirenz+lamivudine, efavirenz+zidovudine or efavirenz+indinavir.

The production method of the crystal or mixed crystal of compound A of the present invention is not particularly lim-

EXAMPLES

While the production method of the crystal of compound A of the present invention is explained in the following by referring to Examples, which are mere examples and do not limit the present invention in any way.

Reference Example 1

Production of Crystal Form I of the Compound A

Step 1

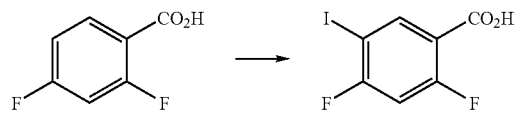

2,4-Difluorobenzoic acid (50 g, 316 mmol) was dissolved in concentrated sulfuric acid (200 ml), and N-iodosuccinimide (68 g, 300 mmol) was added by portions at not more than 5° C. After the completion of the addition, the mixture was stirred at the same temperature for 4.5 hr. The reaction mixture was poured into ice water (ca. 600 ml), then 10% aqueous sodium sulfite solution was added, and the mixture was stirred. The precipitated solid was collected by filtration, washed with water, and vacuum dried to give crude crystals (85 g). The crude crystals obtained in the same manner were combined (total amount 205 g), and recrystallized from 50% aqueous ethanol (820 ml) to give 2,4-difluoro-5-iodobenzoic acid (148 g, yield 73%) as a white solid.

$^1$H NMR (CDCl$_3$ 300 MHz) (σ) ppm: 6.94 (1H, dd, J=10.3, 10.3 Hz), 8.46 (1H, d, J=7.5 Hz)

Step 2

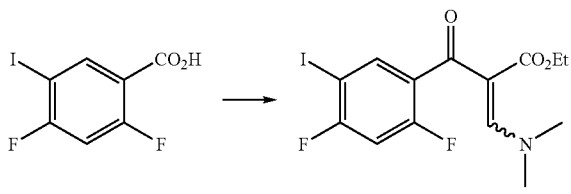

The compound (148 g, 521 mmol) obtained in Step 1 was dissolved in toluene (750 ml), thionyl chloride (76 ml, 1.04 mol) and dimethylformamide (catalytic amount) were added, and the mixture was heated under reflux for 2 hr. The insoluble material was filtered off at 60° C., and the filtrate was concentrated under reduced pressure and azeotroped with toluene (330 ml). The residue was dissolved in tetrahydrofuran (400 ml), and this solution was added dropwise to a solution of ethyl 3,3-dimethylaminoacrylate (82 g, 573 mmol) and triethylamine (87 ml, 625 mmol) in tetrahydrofuran (400 ml), and the mixture was heated under reflux for 7 hr. The reaction mixture was allowed to cool to room temperature, and concentrated under reduced pressure. Water (700 ml) and ethyl acetate (800 ml) were added for partitioning. The organic layer was washed successively with saturated aqueous sodium hydrogen carbonate (250 ml, X2), water (300 ml) and saturated brine (300 ml), and dried over sodium sulfate. After filtration of insoluble material, the filtrate was concentrated under reduced pressure to give a crude product (210 g) of 2-(2,4-difluoro-5-iodobenzoyl)-3-dimethylaminoacrylic acid ethyl ester as a brown solid.

Step 3

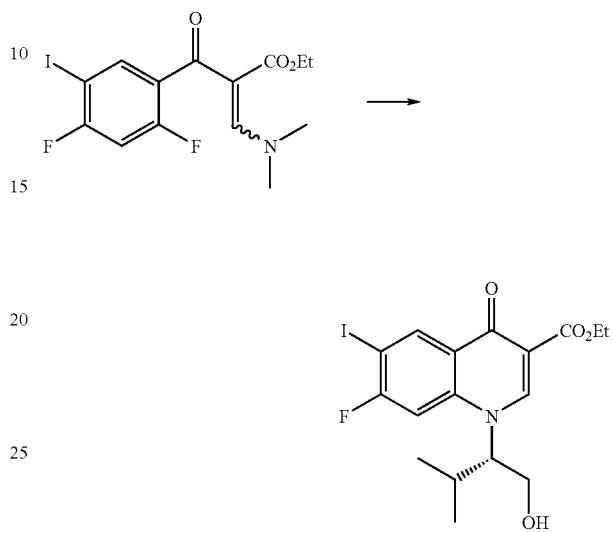

The crude product (210 g) obtained in Step 2 was dissolved in tetrahydrofuran (500 ml), (S)-(+)-valinol (54 g, 521 mmol) was added, and the mixture was stirred at room temperature for 30 min. The reaction mixture was concentrated under reduced pressure, and the residue was dissolved in dimethylformamide (600 ml). Potassium carbonate (144 g, 1.04 mol) was added, and the mixture was stirred with heating at 70° C. for 2 hr. The reaction mixture was allowed to cool to room temperature, added to water (1500 ml) and the mixture was stirred. The precipitated solid was collected by filtration. The obtained solid was washed successively with 30% aqueous ethanol (500 ml) and a mixed solvent of diethyl ether (150 ml) and hexane (150 ml), and vacuum dried to give 7-fluoro-1-((S)-1-hydroxymethyl-2-methylpropyl)-6-iodo-4-oxo-1,4-dihydroquinoline-3-carboxylic acid ethyl ester (178 g, yield 76% (relative to Step 2)) as a beige solid.

$^1$H NMR (DMSO-d$_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS(ESI): M+448

Step 4

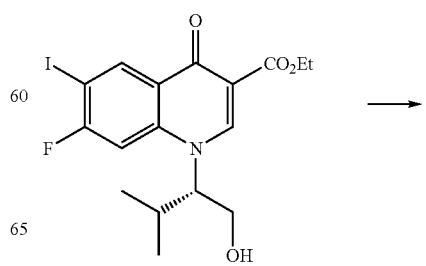

-continued

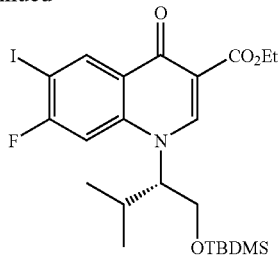

wherein TBDMS means a tert-butyldimethylsilyl group.

The compound (80 g, 179 mmol) obtained in Step 3 was dissolved in dimethylformamide (320 ml), imidazole (16 g, 233 mmol) and tert-butyldimethylsilyl chloride (30 g, 197 mmol) were added, and the mixture was stirred at room temperature for 1.5 hr. Water was added to the reaction mixture and the mixture was extracted with ethyl acetate. The organic layer was washed successively with saturated aqueous ammonium chloride solution and saturated brine, and dried over sodium sulfate. The organic layer was filtered and the filtrate was concentrated under reduced pressure. The obtained residue was purified by silica gel chromatography (ethyl acetate:hexane=1:3 to 1:2) to give 1-((S)-1-tert-butyldimethylsilyloxymethyl-2-methylpropyl)-7-fluoro-6-iodo-4-oxo-1,4-dihydroquinoline-3-carboxylic acid ethyl ester (77 g, yield 77%) as a colorless amorphous form.

$^1$H NMR (CDCl$_3$ 400 MHz) (δ) ppm: −0.07 (3H, s), −0.05 (3H, s), 0.77 (9H, s), 0.84 (3H, d, J=6.5 Hz), 1.18 (3H, d, J=6.5 Hz), 1.40 (3H, t, J=7.2 Hz), 2.35-2.50 (1H, m), 3.85-3.95 (1H, m), 3.98-4.10 (2H, m), 4.30-4.40 (2H, m), 7.26 (1H,s), 8.64 (1H, s), 8.94 (1H, d, J=7.2 Hz)

MS(ESI): M+562

Step 5

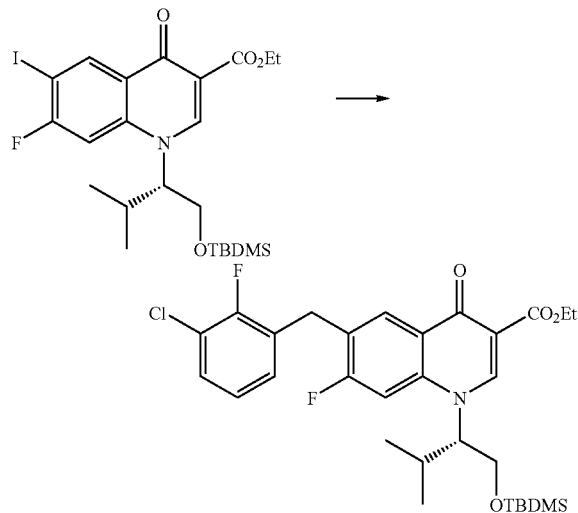

Preparation of a solution of
3-chloro-2-fluorobenzylzinc bromide in
tetrahydrofuran Under an argon stream, zinc powder (11 g, 267 mmol) was suspended in tetrahydrofuran (30 ml), 1,2-dibromoethane (0.15 ml, 1.8 mmol) and trimethylsilyl chloride (0.45 ml, 3.6 mmol) were added at 65° C., and the mixture was stirred with heating for 30 min. A solution of 3-chloro-2-fluorobenzyl bromide (41 g, 178 mmol) in tetrahydrofuran (100 ml) was added dropwise at 65° C., and the mixture was stirred with heating for 2 hr and allowed to cool to room temperature to give a solution of 1M 3-chloro-2-fluorobenzylzinc bromide in tetrahydrofuran. This was used in the next main step.

Main Step

The compound (76 g, 136 mmol) obtained in Step 4 was dissolved in tetrahydrofuran (600 ml) and, under an argon stream, dibenzylidenacetonepalladium(II) (3.2 g, 5.5 mmol) and trifurylphosphine (2.6 g, 11.0 mmol) were added, and a solution of the aforementioned 1M 3-chloro-2-fluorobenzylzinc bromide in tetrahydrofuran (178 ml, 178 mmol) was added dropwise at 60° C. After the completion of the dropwise addition, the mixture was stirred with heating at the same temperature for 2 hr. The reaction mixture was allowed to cool to room temperature, saturated aqueous ammonium chloride solution was added, and the mixture was filtered through celite. The filtrate was extracted twice with ethyl acetate. The organic layer was washed successively with water (twice) and saturated brine, and dried over magnesium sulfate. The organic layer was filtered and the filtrate was concentrated under reduced pressure, and the obtained residue was purified by silica gel chromatography (chloroform: acetone=40:1) to give 1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester (68 g, yield 84%) as a colorless amorphous form.

$^1$H NMR (CDCl$_3$ 400 MHz) (δ) ppm: −0.09 (3H, s), −0.05 (3H, s), 0.75 (9H, s), 0.85 (3H, d, J=6.7 Hz), 1.18 (3H, d, 6.7 Hz), 1.39 (3H, t, J=7.1 Hz), 2.45 (1H, br), 3.89-3.92 (1H, m), 3.98-4.02 (1H, m), 4.07-4.12 (1H, m), 4.12 (2H, s), 4.34-4.41 (2H, m), 6.96-7.00 (1H, m), 7.03-7.05 (1H, m), 7.21-7.24 (1H, m), 7.26-7.29 (1H, m), 8.39 (1H, d, J=8.8 Hz), 8.63 (1H, s)

Step 6

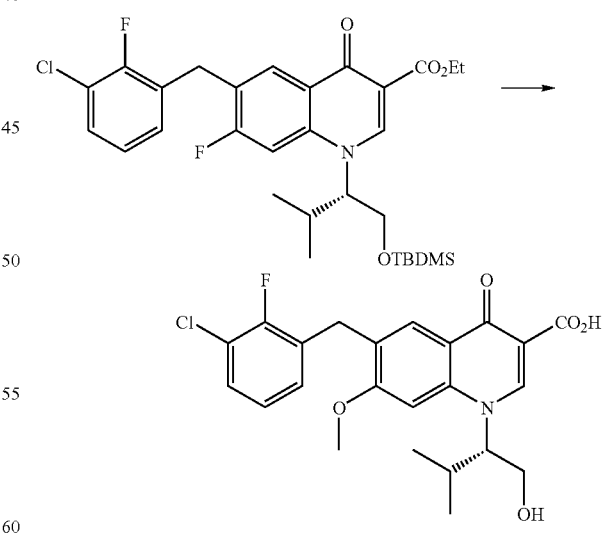

The compound (48 g, 86 mmol) obtained in Step 5 was dissolved in methanol (300 ml), water (5 ml) and 28% sodium methoxide methanol solution (176 ml, 862 mmol) were added, and the mixture was heated under reflux for 24 hr. The reaction mixture was allowed to cool to room temperature and the mixture was neutralized by adding 6N hydrochloric acid.

Methanol was evaporated under reduced pressure. Water was added to the obtained solution and the mixture was stirred. The precipitated solid was collected by filtration and the obtained solid was dissolved in ethyl acetate. The mixture was washed with water and dried over sodium sulfate. The solution was filtered and the filtrate was concentrated under reduced pressure. The obtained residue was recrystallized from ethyl acetate-hexane to give a compound (32 g, yield 86%) as a white solid. The obtained compound (32 g) was dissolved in butyl acetate (160 ml) by heating under reflux, and crystal form II was seeded at 75° C. The mixture was stirred for 3.5 hr while allowing to cool as it was. The precipitated solid was collected by filtration, washed with butyl acetate (25 ml) and vacuum dried to give a compound (25 g, yield 77%) as a white solid. The obtained compound (4.0 g) was dissolved in methanol (40 ml) by heating under reflux at 50° C., and added dropwise to water (40 ml) at room temperature. The mixture was stirred at room temperature for 16 hr, filtered, and the remaining solid was washed with 66% aqueous methanol, and vacuum dried to give a crystal of compound A (crystal form I) (3.9 g, yield 97%) as a white solid.

m.p. 151-152° C.

$^1$H NMR (DMSO-$d_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H,s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Example 1

Production of Crystal Form II of the Compound A

Step 1

2,4-Difluorobenzoic acid (50 g, 316 mmol) was dissolved in concentrated sulfuric acid (200 ml), and N-iodosuccinimide (68 g, 300 mmol) was added by portions at not more than 5° C. After the completion of the addition, the mixture was stirred at the same temperature for 4.5 hr. The reaction mixture was poured into ice water (ca. 600 ml), then 10% aqueous sodium sulfite solution was added, and the mixture was stirred. The precipitated solid was collected by filtration, washed with water, and vacuum dried to give crude crystals (85 g). The crude crystals obtained in the same manner were combined (total amount 205 g), and recrystallized from 50% aqueous ethanol (820 ml) to give 2,4-difluoro-5-iodobenzoic acid (148 g, yield 73%) as a white solid.

$^1$H NMR (CDCl$_3$ 300 MHz) (σ) ppm: 6.94 (1H, dd, J=10.3, 10.3 Hz), 8.46 (1H, d, J=7.5 Hz)

Step 2

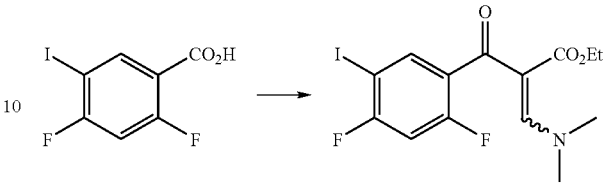

The compound (148 g, 521 mmol) obtained in Step 1 was dissolved in toluene (750 ml), thionyl chloride (76 ml, 1.04 mol) and dimethylformamide (catalytic amount) were added, and the mixture was heated under reflux for 2 hr. The insoluble material was filtered off at 60° C., and the filtrate was concentrated under reduced pressure and azeoptoped with toluene (330 ml). The residue was dissolved in tetrahydrofuran (400 ml), and this solution was added dropwise to a solution of ethyl 3,3-dimethylaminoacrylate (82 g, 573 mmol) and triethylamine (87 ml, 625 mmol) in tetrahydrofuran (400 ml), and the mixture was heated under reflux for 7 hr. The reaction mixture was allowed to cool to room temperature and concentrated under reduced pressure. Water (700 ml) and ethyl acetate (800 ml) were added to allow partitioning. The organic layer was washed successively with saturated aqueous sodium hydrogen carbonate (250 ml) twice, water (300 ml) and saturated brine (300 ml), and dried over sodium sulfate. The mixture was filtered, and the filtrate was concentrated under reduced pressure to give a crude product (210 g) of 2-(2,4-difluoro-5-iodobenzoyl)-3-dimethylaminoacrylic acid ethyl ester as a brown solid.

Step 3

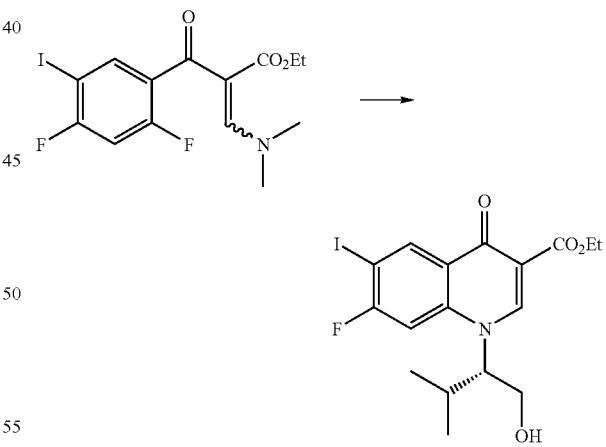

The crude product (210 g) obtained in Step 2 was dissolved in tetrahydrofuran (500 ml), (S)-(+)-valinol (54 g, 521 mmol) was added, and the mixture was stirred at room temperature for 30 min. The reaction mixture was concentrated under reduced pressure, and the residue was dissolved in dimethylformamide (600 ml). Potassium carbonate (144 g, 1.04 mol) was added, and the mixture was stirred with heating at 70° C. for 2 hr. The reaction mixture was allowed to cool to room temperature, added to water (1500 ml) and the mixture was stirred. The precipitated solid was collected by filtration. The obtained solid was washed successively with 30% aqueous ethanol (500 ml) and a mixed solvent of diethyl ether (150 ml) and hexane (150 ml), and vacuum dried to give 7-fluoro-1-((S)-1-hydroxymethyl-2-methylpropyl)-6-iodo-4-oxo-1,4-dihydroquinoline-3-carboxylic acid ethyl ester (178 g, yield 76% (relative to Step 2)) as a beige solid.

$^1$H NMR (DMSO-d$_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS(ESI): M+448

Step 4

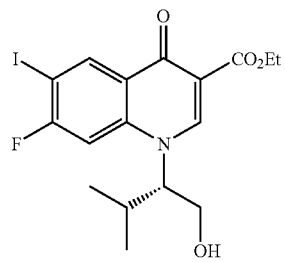

The compound (150 g, 335 mmol) obtained in Step 3 was dissolved in dimethylformamide (500 ml), imidazole (30 g, 436 mmol) and tert-butyldimethylsilyl chloride (56 g, 369 mmol) were added, and the mixture was stirred at room temperature for 1.5 hr. Water was added to the reaction mixture and extracted with ethyl acetate. The organic layer was washed successively with water, saturated aqueous ammonium chloride solution and saturated brine, and dried over sodium sulfate. The organic layer was filtered and the filtrate was concentrated under reduced pressure, and the obtained residue was purified by silica gel chromatography (ethyl acetate:hexane=1:3 to 1:2) to give 1-((S)-1-tert-butyldimethylsilyloxymethyl-2-methylpropyl)-7-fluoro-6-iodo-4-oxo-1,4-dihydroquinoline-3-carboxylic acid ethyl ester (173 g, yield 92%) as a colorless amorphous form.

$^1$H NMR (CDCl$_3$ 400 MHz) (δ) ppm: −0.07 (3H, s), −0.05 (3H, s), 0.77 (9H, s), 0.84 (3H, d, J=6.5 Hz), 1.18 (3H, d, J=6.5 Hz), 1.40 (3H, t, J=7.2 Hz), 2.35-2.50 (1H, m), 3.85-3.95 (1H, m), 3.98-4.10 (2H, m), 4.30-4.40 (2H, m), 7.26 (1H, s), 8.64 (1H, s), 8.94 (1H, d, J=7.2 Hz)

MS(ESI): M+562

Step 5

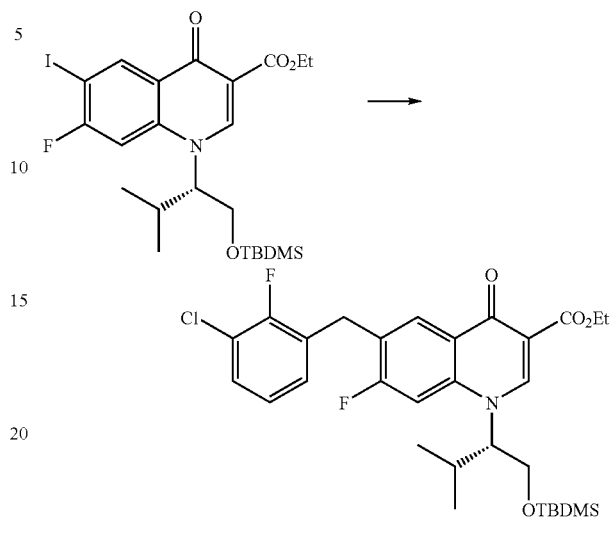

Preparation of a solution of 3-chloro-2-fluorobenzylzinc bromide in tetrahydrofuran Under an argon stream, zinc powder (11 g, 175 mmol) was suspended in tetrahydrofuran (30 ml), 1,2-dibromoethane (0.1 ml, 1.20 mmol) and trimethylsilyl chloride (0.29 ml, 2.4 mmol) were added at 60° C., and the mixture was stirred with heating for 30 min. A solution of 3-chloro-2-fluorobenzyl bromide (27 g, 119 mmol) in tetrahydrofuran (60 ml) was added dropwise at 60° C. The mixture was stirred with heating for 1 hr and allowed to cool to room temperature to give a solution of 1M 3-chloro-2-fluorobenzylzinc bromide in tetrahydrofuran. This was used in the next main step.

Main Step

The compound (50 g, 89 mmol) obtained in Step 4 was dissolved in tetrahydrofuran (400 ml) and, under an argon stream, dichlorobis(triphenylphosphine)palladium(II) (2.1 g, 3.6 mmol) was added and a solution of the above-mentioned 1M 3-chloro-2-fluorobenzylzinc bromide in tetrahydrofuran was added dropwise at 60° C. After the completion of the dropwise addition, the mixture was stirred with heating at the same temperature for 1.5 hr. The reaction mixture was allowed to cool to room temperature, 1N hydrochloric acid was added and the mixture was extracted 3 times with ethyl acetate. The organic layer was washed successively with water and saturated brine, and dried over magnesium sulfate. The organic layer was filtered and the filtrate was concentrated under reduced pressure, and the obtained residue was purified by silica gel chromatography (ethyl acetate:hexane=1:2 to 1:1) to give 1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester (43 g, yield 83%) as a brown amorphous form.

$^1$H NMR (CDCl$_3$ 400 MHz) (δ) ppm: −0.09 (3H, s), −0.05 (3H, s), 0.75 (9H, s), 0.85 (3H, d, J=6.7 Hz), 1.18 (3H, d, 6.7 Hz), 1.39 (3H, t, J=7.1 Hz), 2.45 (1H, br), 3.89-3.92 (1H, m), 3.98-4.02 (1H, m), 4.07-4.12 (1H, m), 4.12 (2H, s), 4.34-4.41 (2H, m), 6.96-7.00 (1H, m), 7.03-7.05 (1H, m), 7.21-7.24 (1H, m), 7.26-7.29 (1H, m), 8.39 (1H, d, J=8.8 Hz), 8.63 (1H, s)

Step 6

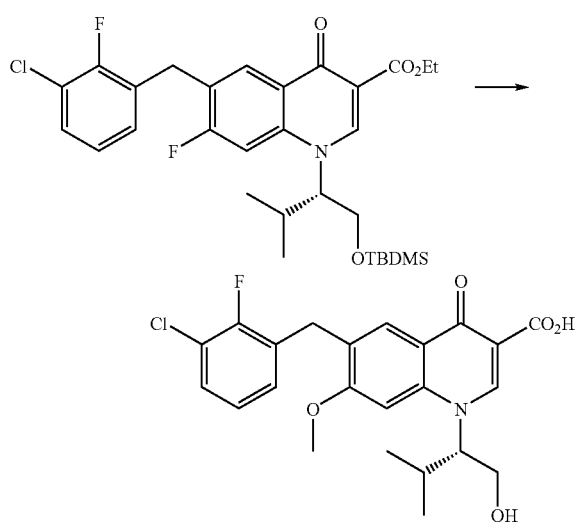

The compound (43 g, 74 mmol) obtained in Step 5 was dissolved in methanol (280 ml), 28% sodium methoxide methanol solution (151 ml, 742 mmol) and water (4.3 ml) were added, and the mixture was heated under reflux for 20 hr. The reaction mixture was filtered through celite. The filtrate was concentrated under reduced pressure. Water (400 ml) was added to the residue, and the mixture was washed with hexane (100 ml). The aqueous layer was acidified by adding concentrated hydrochloric acid (65 ml), and the mixture was extracted with ethyl acetate. The organic layer was washed successively with water and saturated brine, and dried over sodium sulfate. The solution was filtered and the filtrate was concentrated under reduced pressure. The obtained crude product (35 g, brown oil) was dissolved in ethyl acetate (49 ml) by heating under reflux, hexane (30 ml) was added while allowing to cool, and the mixture was stirred for 18.5 hr. The precipitated solid was collected by filtration, washed with a mixed solvent of ethyl acetate and hexane (1:1), and vacuum dried to give a crystal of compound A (crystal form II) (27 g, yield 82%) as a white solid.

m.p. 153.7-153.9° C.

$^1$H NMR (DMSO-d$_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H,s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Example 2

Production of Crystal Form II of the Compound A

Example 2-1

Production of Crystal Form II of the Compound A

Step 1

2,4-Difluorobenzoic acid (100 g, 633 mmol) was dissolved in concentrated sulfuric acid (400 ml), and N-iodosuccinimide (142 g, 601 mol) was added by portions at not more than 5° C. After the completion of the addition, the mixture was stirred at the same temperature for 6 hr. The reaction mixture was poured into ice water (ca. 2400 ml), then saturated aqueous sodium sulfite solution was added, and the mixture was stirred. The precipitated solid was collected by filtration, washed with water, and vacuum dried to give crude crystals (188 g). The crude crystals obtained in the same manner were combined (total amount 568 g), and recrystallized from 50% aqueous ethanol (2600 ml) to give 2,4-difluoro-5-iodobenzoic acid (388 g, yield 68%) as a white solid.

$^1$H NMR (CDCl$_3$ 300 MHz) (σ) ppm: 6.94 (1H, dd, J=10.3, 10.3 Hz), 8.46 (1H, d, J=7.5 Hz)

Step 2

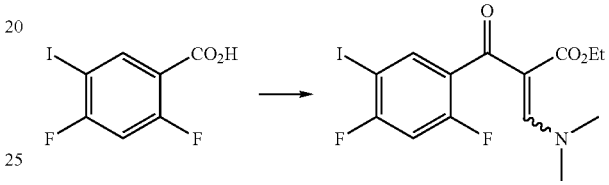

The compound (200 g, 704 mmol) obtained in Step 1 was dissolved in toluene (1000 ml), thionyl chloride (103 ml, 408 mmol) and dimethylformamide (catalytic amount) were added, and the mixture was heated under reflux for 2 hr. The insoluble material was filtered off, and the filtrate was concentrated under reduced pressure and azeotroped with toluene. The residue was dissolved in tetrahydrofuran (500 ml), this solution was added dropwise to a solution of ethyl 3,3-dimethylaminoacrylate (111 g, 775 mmol) and triethylamine (118 ml, 845 mmol) in tetrahydrofuran (500 ml), and the mixture was heated under reflux for 3 hr. The reaction mixture was allowed to cool to room temperature and filtered and the filtrate was concentrated under reduced pressure. Water (500 ml) and ethyl acetate (800 ml) were added to allow partitioning. The organic layer was washed successively with saturated aqueous sodium hydrogen carbonate (200 ml), water (200 ml) and saturated brine, and dried over sodium sulfate. The organic layer was filtered, and the filtrate was concentrated under reduced pressure to give a crude product (273 g) of 2-(2,4-difluoro-5-iodobenzoyl)-3-dimethylaminoacrylic acid ethyl ester as a brown solid.

Step 3

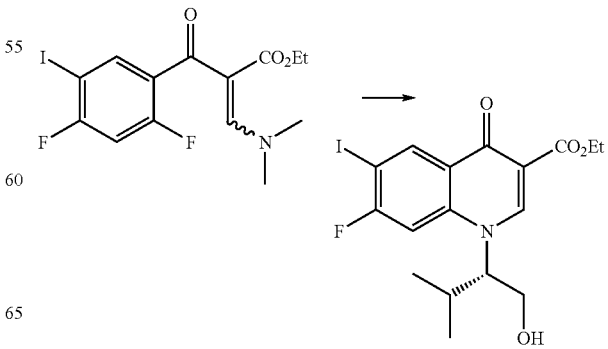

The crude product (273 g) obtained in Step 2 was dissolved in tetrahydrofuran (650 ml), (S)-(+)-valinol (73 g, 708 mmol) was added, and the mixture was stirred at room temperature for 2 hr. The reaction mixture was concentrated under reduced pressure and the residue was dissolved in dimethylformamide (800 ml). Potassium carbonate (195 g 1.41 mol) was added, and the mixture was stirred with heating at 70° C. for 2.5 hr. The reaction mixture was allowed to cool to room temperature, added to water (2000 ml) and the mixture was stirred. The precipitated solid was collected by filtration. The obtained solid was subject to slurry washing successively with water and 30% aqueous ethanol (650 ml) and vacuum dried to give a crude product (217 g). The obtained crude product (217 g) was subject to slurry washing with a mixed solvent of ethyl acetate (650 ml) and hexane (440 ml) with heating under reflux. The mixture was filtered, and the remaining solid was vacuum dried to give 7-fluoro-1-((S)-1-hydroxymethyl-2-methylpropyl)-6-iodo-4-oxo-1,4-dihydroquinoline-3-carboxylic acid ethyl ester (207 g, yield 66% (relative to Step 2)) as a pale-brown solid.

$^1$H NMR (DMSO-$d_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS(ESI): M+448

Step 4

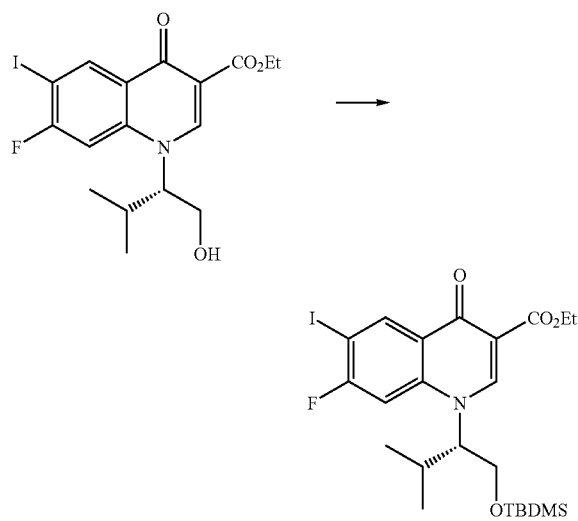

The compound (150 g, 335 mmol) obtained in Step 3 was dissolved in dimethylformamide (450 ml), imidazole (27 g, 397 mmol) and tert-butyldimethylsilyl chloride (58 g, 385 mmol) were added, and the mixture was stirred overnight at room temperature. Water (900 ml) was added to the reaction mixture, and the mixture was extracted with ethyl acetate (680 ml). The organic layer was washed successively with water (450 ml, 3 times) and saturated brine (200 ml), and dried over sodium sulfate. The organic layer was filtered, and the filtrate was concentrated under reduced pressure to give a crude product (192 g) of 1-((S)-1-tert-butyldimethylsilyloxymethyl-2-methylpropyl)-7-fluoro-6-iodo-4-oxo-1,4-dihydroquinoline-3-carboxylic acid ethyl ester as a pale-yellow amorphous form.

Step 5

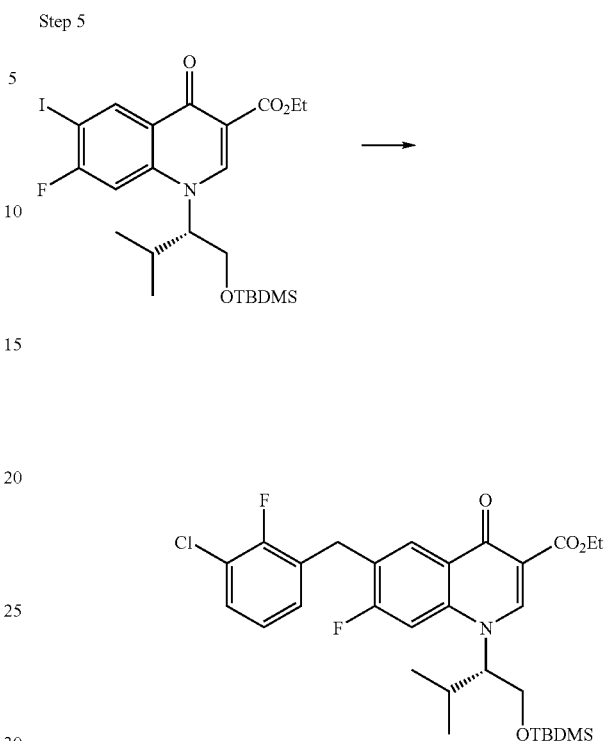

The crude product (162 g) obtained in Step 4 was dissolved in tetrahydrofuran (160 ml) and, under an argon stream, dibenzylideneacetone palladium(II) (1.7 g, 2.9 mmol) and tri-furylphosphine (1.3 g, 5.8 mmol) were added. To this mixture was added dropwise at 60° C. a solution of (375 ml, 375 mmol) of 1M 3-chloro-2-fluorobenzylzinc bromide in tetrahydrofuran obtained in the same manner as in Example 1, Step 5 and, after the completion of the dropwise addition, the mixture was stirred with heating at the same temperature for 3.5 hr. The reaction is mixture was allowed to cool to room temperature, ethyl acetate (640 ml) and 10% aqueous citric acid solution (400 ml) were added, and the mixture was filtered through Celite, and the filtrate was partitioned. The organic layer was washed successively with water (200 ml), saturated aqueous sodium hydrogen carbonate (400 ml) and saturated brine (200 ml), and dried over sodium sulfate. The organic layer was filtered, and the filtrate was concentrated under reduced pressure to give a crude product (186 g) of 1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester as a brown oil.

Step 6

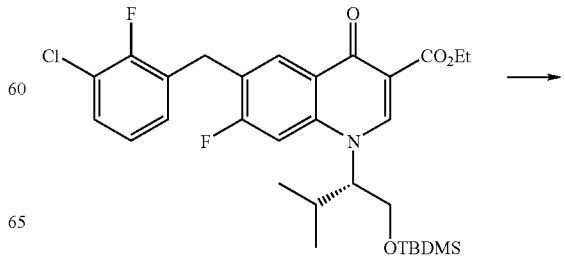

-continued

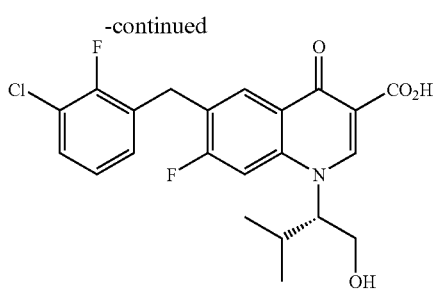

The crude product (193 g) obtained in Step 5 was dissolved in isopropanol (650 ml), 1N aqueous sodium hydroxide solution (1290 ml, 1.29 mol) was added, and the mixture was heated under reflux for 2 hr. The reaction mixture was allowed to cool to room temperature, and filtered through Celite. The filtrate was acidified by adding concentrated hydrochloric acid and the mixture was stirred. The precipitated solid was collected by filtration, and vacuum dried to give a crude product (132 g) as a pale-yellow solid. The crude products obtained in the same manner were combined (total amount 143 g), suspended in butyl acetate (430 ml) and subject to slurry stirring with heating under reflux for 1 hr. The suspension was allowed to cool to room temperature and filtered and vacuum dried to give 6-(3-chloro-2-fluorobenzyl)-7-fluoro-1-((S)-1-hydroxymethyl-2-methylpropyl)-4-oxo-1,4-dihydroquinoline-3-carboxylic acid (99 g, yield 74% (relative to Step 3)) as a gray solid.

$^1$H NMR (DMSO-$d_6$ 400 MHz) (δ) ppm: 0.71 (3H, d, J=6.5 Hz), 1.13 (3H, d, J=6.5 Hz), 2.36 (1H, br), 3.77 (1H, br), 3.94 (1H, br), 4.25 (2H, s), 4.77 (1H, br), 5.16 (1H, t, J=2.4 Hz), 7.19-7.23 (1H, m), 7.32-7.35 (1H, m), 7.48-7.52 (1H, m), 8.24-8.28 (2H, m), 9.00 (1H, s), 15.00 (1H, s)

MS(ESI): M+436

Step 7

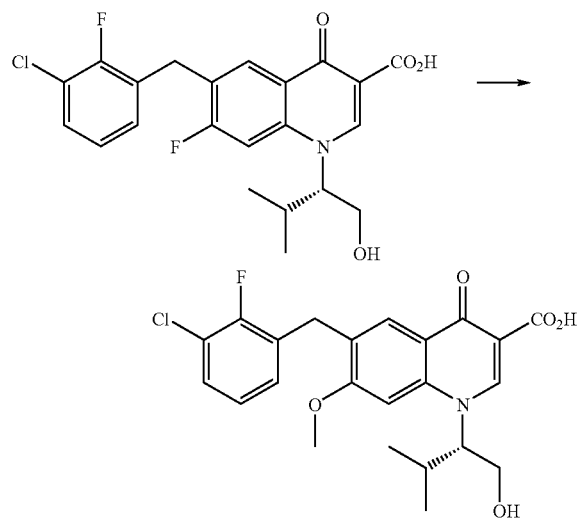

The compound (99 g, 227 mmol) obtained in Step 6 was dissolved in methanol (530 ml), 28% sodium methoxide methanol solution (465 ml, 2.28 mol) was added, and the mixture was heated under reflux for 20 hr. The reaction mixture was allowed to cool to room temperature and filtered through Celite. The filtrate was concentrated under reduced pressure. The residue was acidified by adding water (200 ml) and concentrated hydrochloric acid (190 ml), and extracted with ethyl acetate (500 ml). The organic layer was washed twice with water (200 ml), and dried over sodium sulfate. The mixture was filtered, and the filtrate was concentrated under reduced pressure to give a crude product (108 g). The obtained crude product (108 g) was dissolved in isobutyl acetate (330 ml) with heating and the mixture was stirred while allowing to cool for 24 hr. The precipitated solid was collected by filtration, and vacuum dried to give compound A (71 g, yield 69%) as a white solid. The crude crystals obtained in the same manner were combined (total amount 233 g), dissolved in isobutyl acetate (470 ml) by heating under reflux, and the mixture was stirred overnight while allowing to cool. The precipitated solid was collected by filtration, and vacuum dried to give a crystal of compound A (crystal form II) (206 g, yield 88%) as a white solid.

$^1$H NMR (DMSO-$d_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H, s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Example 2-2

Production of Crystal Form II of the Compound A

Step 1

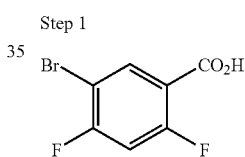

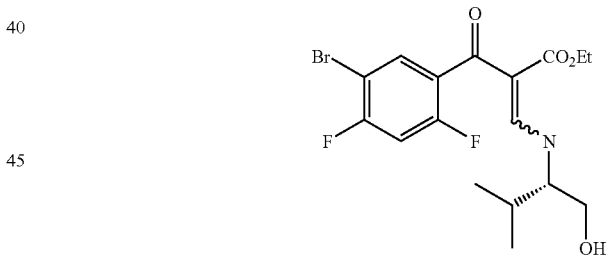

5-Bromo-2,4-difluorobenzoic acid (82.7 kg, 349 mol) was dissolved in toluene (420 L), thionyl chloride (62.3 kg, 523 mol) and dimethylformamide (catalytic amount) were added, and the mixture was stirred at 70° C. for 6 hr. The reaction mixture was allowed to cool to room temperature, concentrated under reduced pressure, and azeotroped again with toluene (420 L). The residue was dissolved in toluene (220 L), this solution was added dropwise to a solution of ethyl 3,3-dimethylaminoacrylate (55.0 kg, 384 mol) and diisopropylethylamine (58.6 kg, 523 mol) in toluene (220 L), and the mixture was stirred with heating at 70° C. for 21 hr. The reaction mixture was allowed to cool to room temperature, (S)-(+)-valinol (36.0 kg, 349 mol) was added, and the mixture was stirred at room temperature for 1.5 hr. Water (420 L) was added to the reaction mixture to allow partitioning, and the organic layer was washed successively with 1N hydrochloric acid (250 L, twice), water (420 L), 5% aqueous sodium hydrogen carbonate (250 L, twice), water (420 L) and 10% brine (250 L). The extract was concentrated under reduced pressure and azeotroped with dimethylformamide (420 L) to give a concentration residue (330 L) containing a crude product of 2-(5-bromo-2,4-difluorobenzoyl)-3-((S)-1-hydroxymethyl-2-methylpropylmethylamino)acrylic acid ethyl ester.

Step 2

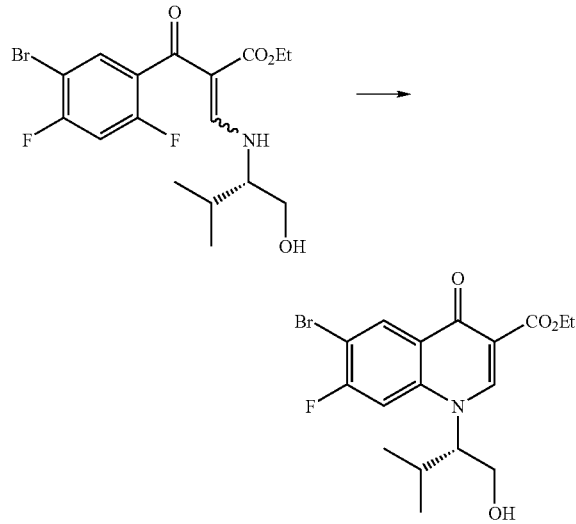

To a solution (330 L) of the crude product obtained in Step 1 in dimethylformamide was added 1,8-diazabicyclo[5.4.0] undecane (105 kg, 349 mol) and the mixture was stirred at room temperature for 23 hr. To the reaction mixture were added dimethylformamide (330 L), and then water (170 L) and, after stirring for 2 hr, water (170 L) was added dropwise. The precipitated solid was collected by filtration and washed with dimethylformamide (170 L)-water (170 L) mixture, and then with ethanol (460 L)-water (200 L) mixed solution. The obtained solid was vacuum dried, suspended in an ethyl acetate (330 L)-n-heptane (330 L) mixture and subject to slurry washing. The suspension was filtered, and the remaining solid was vacuum dried to give 6-bromo-7-fluoro-1-((S)-1-hydroxymethyl-2-methylpropyl)-4-oxo-1,4-dihydroquinoline-3-carboxylic acid ethyl ester (102 kg, yield 73%) as a yellow white solid. This compound was confirmed to be equivalent to the standard product of the compound by high performance liquid chromatography (HPLC) analysis.

Step 3

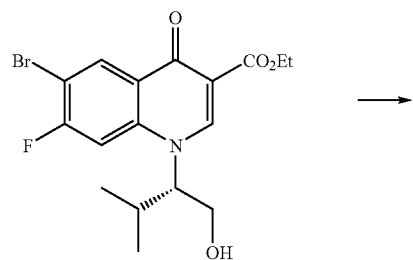

-continued

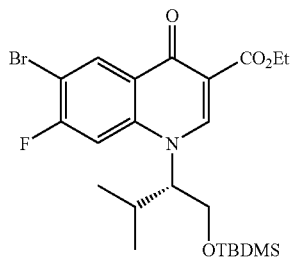

The compound (45.0 kg, 112 mol) obtained in Step 2 and imidazole (9.95 kg, 146 mol) were suspended in toluene (180 L), a solution of tert-butyldimethylsilyl chloride (17.8 kg, 118 mol) in toluene (45 L) was added at 50° C., and the mixture was stirred at the same temperature for 3 hr. Toluene (230 L) was added to the reaction mixture, and washed successively with water (450 L, twice) and 20% brine (450 L). The extract was concentrated under reduced pressure and azeotroped with tetrahydrofuran (320 L) to give a concentration residue (390 L) containing a crude product of 6-bromo-1-((S)-1-tert-butyldimethylsilyloxymethyl-2-methylpropyl)-7-fluoro-4-oxo-1,4-dihydroquinoline-3-carboxylic acid ethyl ester.

Step 4

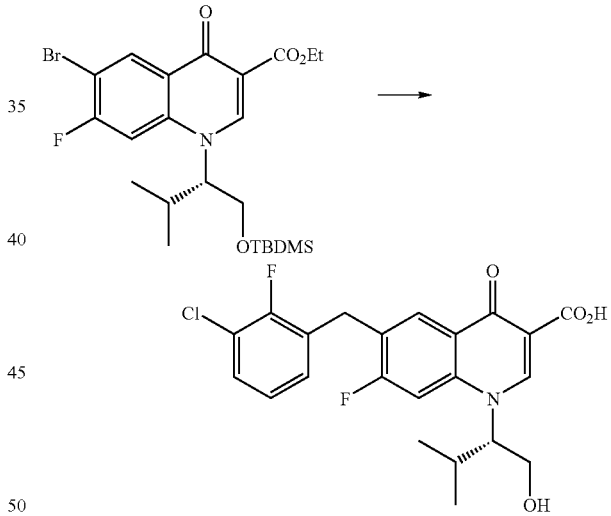

Preparation of a solution of 3-chloro-2-fluorobenzylzinc bromide in tetrahydrofuran Under a nitrogen stream, zinc powder (18.8 kg, 287 mol) was suspended in tetrahydrofuran (130 L), 1,2-dibromoethane (470 g, 2.50 mol) was added at 60° C., and the mixture was stirred at the same temperature for 30 min. Trimethylsilyl chloride (560 g, 3.10 mol) was added to this suspension at room temperature, and the mixture was stirred with heating for 30 min. A solution of 3-chloro-2-fluorobenzyl bromide (54.0 kg, 242 mol) in tetrahydrofuran (65 L) was added dropwise at 0° C., and the mixture was stirred at 20° C. for 3 hr.

The remaining zinc was filtered off to give a solution of 1M 3-chloro-2-fluorobenzylzinc bromide in tetrahydrofuran. This was used in the next main step.

Main Step

Under a nitrogen stream, tris(dibenzylidenacetone)dipalladium(0) (1.96 kg, 3.36 mol) and triphenylphosphine (1.77 kg, 6.72 mol) were dissolved in tetrahydrofuran (180 L), and the mixture was stirred at room temperature for 1 hr. A solution (390 L) of the crude product obtained in Step 3 in tetrahydrofuran was added dropwise at room temperature and washed with tetrahydrofuran (45 L). A solution (164 kg, 157 mol) of the above-mentioned 1M 3-chloro-2-fluorobenzylzinc bromide in tetrahydrofuran prepared in advance was added dropwise at room temperature, and the mixture was stirred with heating at 55° C. for 5 hr. The reaction mixture was allowed to cool to room temperature, toluene (230 L) and 25% aqueous ammonium chloride solution (230 L) were added and the mixture was stirred. After filtration, the mixture was partitioned. The organic layer was washed successively with 25% aqueous ammonium chloride solution (230 L), water (230 L), 5% aqueous sodium hydrogen carbonate (230 L, 3 times) and 10% brine (230 L). The extract was concentrated under reduced pressure to give a crude product (80 L) of 6-(3-chloro-2-fluorobenzyl)-7-fluoro-1-((S)-1-hydroxymethyl-2-methylpropyl)-4-oxo-1,4-dihydroquinoline-3-carboxylic acid as a brown oil.

Step 5

The crude product (80 L) obtained in Step 4 was dissolved in isopropanol (180 L), 1N aqueous sodium hydroxide solution (180 L, 180 mol) was added, and the mixture was stirred with heating at 50° C. for 9 hr. Activated carbon (4.5 kg) was added to the reaction mixture. The mixture was stirred at room temperature for 30 min, filtered through cellulose powder and thoroughly washed with an isopropanol (45 L)—water (45 L) mixture. Water (180 L) and n-heptane (230 L) were added to the filtrate and, after stirring, the mixture was partitioned. The aqueous layer was washed again with n-heptane (230 L). 4N Hydrochloric acid (45 L, 180 mol) and methyl isopropyl ketone (450 L) were added to the organic layer and, after stirring, the mixture was partitioned. The organic layer was washed successively with 10% brine (230 L), twice with 8.5% aqueous sodium hydrogen carbonate (230 L), 0.5N hydrochloric acid (230 L) and water (230 L). The extract was concentrated under reduced pressure, azeotroped 3 times with toluene (230 L). The residue was stirred at 100° C. for 1.5 hr, allowed to cool to room temperature and stirred for 3 hr. The precipitated solid was collected by filtration and the obtained solid was washed with toluene (45 L) and vacuum dried to give 6-(3-chloro-2-fluorobenzyl)-7-fluoro-1-[(S)-1-hydroxymethyl-2-methylpropyl]-4-oxo-1,4-dihydroquinoline-3-carboxylic acid (42.5 kg, yield 87%) as a pale-yellow solid. This compound was confirmed to be equivalent to the standard product by HPLC analysis.

Step 6

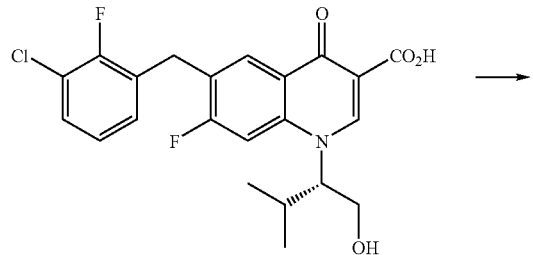

-continued

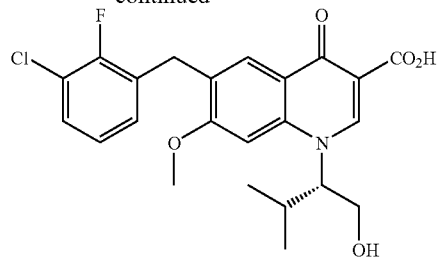

The compound (39.2 kg, 89.9 mol) obtained in Step 5 was dissolved in methanol (240 L), 28% sodium methoxide methanol solution (173 kg, 899 mol) was added dropwise at 10° C., and the mixture was stirred with heating at 70° C. for 21 hr. Activated carbon (3.9 kg) was added to the reaction mixture. The mixture was stirred at room temperature for 1 hr, filtered through cellulose powder and thoroughly washed with methanol (80 L). Water (29 kg, 1620 mol) was added to the filtrate and the mixture was concentrated under reduced pressure. The residue was azeotroped twice with isopropanol (240 L, 120 L). To the residue were added 15% brine (200 L) and toluene (200 L) and, after stirring, the mixture was partitioned. The organic layer was washed successively with 20% brine (200 L, 3 times), 0.5N hydrochloric acid (200 L) containing sodium chloride (10 kg) and 20% brine (200 L). The organic layer was concentrated under reduced pressure and azeotroped with ethyl acetate (200 L). Ethyl acetate (320 L) and water (200 L) were added to the residue and, after stirring, the mixture was partitioned. The organic layer was concentrated under reduced pressure and azeotroped twice with isobutyl acetate (200 L). The residue was dissolved by heating filtered while it was hot, and thoroughly washed with isobutyl acetate (20 L). A seed crystal (crystal form II of compound A, 39 g) was added to the filtrate at 60° C., and the mixture was stirred at the same temperature for 1.5 hr. The mixture was stirred with heating at 80° C. for 2 hr, allowed to cool to room temperature and further stirred for 6 hr. The precipitated solid was collected by filtration. The obtained solid was washed with isobutyl acetate (40 L) and vacuum dried to give a crystal of compound A (crystal form II) (29.0 kg, yield 72%) as a white solid. This crystal was confirmed to be equivalent to the standard product of the crystal (crystal form II of compound A obtained in Example 2-1) by HPLC and X ray powder diffraction (XRPD) analysis.

Example 2-3

Production of Crystal Form II of the Compound A

The crystal form II can be also produced by crystallization according to the methods described in Examples 2-3-1 to 2-3-26.

Example 2-3-1

The compound A (200 mg) obtained in Example 1 was dissolved in 1-butanol (2 ml) with heating under reflux. The mixture was stirred for 17 hr while allowing to cool. The precipitated solid was collected by filtration and vacuum dried to give crystal form II (125 mg, yield 63%) of compound A as a white solid.

Example 2-3-2

The compound A (200 mg) obtained in Example 1 was dissolved in butyl acetate (2 ml) with heating under reflux. The mixture was stirred for 17 hr while allowing to cool. The precipitated solid was collected by filtration and vacuum dried to give crystal form II (102 mg, yield 51%) of compound A as a white solid.

Example 2-3-3

The compound A (200 mg) obtained in Example 1 was dissolved in methyl isobutyl ketone (2 ml) with heating under reflux. Heptane (2 ml) was added dropwise and the mixture was stirred for 6 hr while allowing to cool. The precipitated solid was collected by filtration and vacuum dried to give crystal form II (168 mg, yield 84%) of compound A as a white solid.

Example 2-3-4

The compound A (200 mg) obtained in Example 1 was dissolved in ethanol (2 ml) with heating under reflux. The mixture was stirred for 17 hr while allowing to cool. The precipitated solid was collected by filtration and vacuum dried to give crystal form II (56 mg, yield 28%) of compound A as a white solid.

Example 2-3-5

The compound A (200 mg) obtained in Example 1 was dissolved in ethyl acetate (2 ml) with heating under reflux. Heptane (1.6 ml) was added dropwise and the mixture was stirred for 6 hr while allowing to cool. The precipitated solid was collected by filtration and vacuum dried to give crystal form II (166 mg, yield 83%) of compound A as a white solid.

Example 2-3-6

The compound A (200 mg) obtained in Example 1 was dissolved in methyl ethyl ketone (2 ml) with heating under reflux. Heptane (4 ml) was added dropwise and the mixture was stirred for 6 hr while allowing to cool. The precipitated solid was collected by filtration and vacuum dried to give crystal form II (123 mg, yield 62%) of compound A as a white solid.

Example 2-3-7

The compound A (200 mg) obtained in Example 1 was dissolved in 1-propanol (2 ml) with heating under reflux. The mixture was stirred for 17 hr while allowing to cool. The precipitated solid was collected by filtration and vacuum dried to give crystal form II (91 mg, yield 46%) of compound A as a white solid.

Example 2-3-8

The compound A (200 mg) obtained in Example 1 was dissolved in isopropanol (2 ml) with heating under reflux. The mixture was stirred for 17 hr while allowing to cool. The precipitated solid was collected by filtration and vacuum dried to give crystal form II (88 mg, yield 44%) of compound A as a white solid.

Example 2-3-9

The compound A (200 mg) obtained in Example 1 was dissolved in cumene (2 ml) with heating under reflux. The mixture was stirred for 17 hr while allowing to cool. The precipitated solid was collected by filtration and vacuum dried to give crystal form II (188 mg, yield 94%) of compound A as a white solid.

Example 2-3-10

The compound A (200 mg) obtained in Example 1 was dissolved in anisole (2 ml) with heating under reflux. The mixture was stirred for 17 hr while allowing to cool. The precipitated solid was collected by filtration and vacuum dried to give crystal form II (107 mg, yield 54%) of compound A as a white solid.

Example 2-3-11

The compound A (200 mg) obtained in Example 1 was dissolved in acetone (2 ml) with heating under reflux. Heptane (2 ml) was added dropwise and the mixture was stirred for 16.5 hr while allowing to cool. Heptane (4 ml) was further added, and the mixture was further stirred for 24 hr. The precipitated solid was collected by filtration and vacuum dried to give crystal form II (134 mg, yield 67%) of compound A as a white solid.

Example 2-3-12

The compound A (200 mg) obtained in Example 1 was dissolved in ethanol (2 ml) with heating under reflux. Heptane (4 ml) was added dropwise and the mixture was stirred for 19 hr while allowing to cool. The precipitated solid was collected by filtration and vacuum dried to give crystal form II (129 mg, yield 65%) of compound A as a white solid.

Example 2-3-13

The compound A (200 mg) obtained in Example 1 was dissolved in isopropanol (2 ml) with heating under reflux. Heptane (4 ml) was added dropwise and the mixture was stirred for 19 hr while allowing to cool. The precipitated solid was collected by filtration and vacuum dried to give crystal form II (166 mg, yield 83%) of compound A as a white solid.

Example 2-3-14

The compound A (200 mg) obtained in Example 1 was dissolved in 1-propanol (2 ml) with heating under reflux. Heptane (4 ml) was added dropwise and the mixture was stirred for 19 hr while allowing to cool. The precipitated solid was collected by filtration and vacuum dried to give crystal form II (158 mg, yield 79%) of compound A as a white solid.

Example 2-3-15

The compound A (200 mg) obtained in Example 1 was dissolved in isobutanol (2 ml) with heating under reflux. The mixture was stirred for 21 hr while allowing to cool. The precipitated solid was collected by filtration and vacuum dried to give crystal form II (131 mg, yield 66%) of compound A as a white solid.

Example 2-3-16

The compound A (200 mg) obtained in Example 1 was dissolved in toluene (2 ml) with heating at 100° C. The mixture was stirred for 37 hr while allowing to cool. The precipitated solid was collected by filtration and vacuum dried to give crystal form II (190 mg, yield 95%) of compound A as a white solid.

Example 2-3-17

The compound A (200 mg) obtained in Example 1 was dissolved in methyl butyl ketone (2 ml) with heating at 60° C. Heptane (1.8 ml) was added dropwise and the mixture was stirred for 37 hr while allowing to cool. The precipitated solid was collected by filtration and vacuum dried to give crystal form II (191 mg, yield 96%) of compound A as a white solid.

Example 2-3-18

The compound A (200 mg) obtained in Example 1 was dissolved in chloroform (1 ml) with heating at 60° C. Isopropyl ether (1.8 ml) was added dropwise and the mixture was stirred for 37 hr while allowing to cool. The precipitated solid was collected by filtration and vacuum dried to give crystal form II (184 mg, yield 92%) of compound A as a white solid.

Example 2-3-19

The compound A (200 mg) obtained in Example 1 was dissolved in tetrahydrofuran (1 ml) by heating at 60° C. Isopropyl ether (2 ml) was added dropwise and the mixture was stirred for 41 hr while allowing to cool. The precipitated solid was collected by filtration and vacuum dried to give crystal form II (144 mg, yield 72%) of compound A as a white solid.

Example 2-3-20

The compound A (200 mg) obtained in Example 1 was dissolved in isobutanol (2 ml) with heating under reflux. Heptane (2 ml) was added dropwise and the mixture was stirred for 21 hr while allowing to cool. The precipitated solid was collected by filtration and vacuum dried to give crystal form II (160 mg, yield 80%) of compound A as a white solid.

Example 2-3-21

The compound A (200 mg) obtained in Example 1 was dissolved in butanol (2 ml) with heating under reflux. Heptane (2 ml) was added dropwise and the mixture was stirred for 21 hr while allowing to cool. The precipitated solid was collected by filtration and vacuum dried to give crystal form II (152 mg, yield 76%) of compound A as a white solid.

Example 2-3-22

The compound A (200 mg) obtained in Example 1 was dissolved in isobutyl acetate (2 ml) with heating under reflux. The mixture was stirred for 21 hr while allowing to cool. The precipitated solid was collected by filtration and vacuum dried to give crystal form II (140 mg, yield 70%) of compound A as a white solid.

Example 2-3-23

The compound A (200 mg) obtained in Example 1 was dissolved in isobutyl acetate (2 ml) with heating under reflux. Heptane (2 ml) was added dropwise and the mixture was stirred for 21 hr while allowing to cool. The precipitated solid was collected by filtration and vacuum dried to give crystal form II (178 mg, yield 89%) of compound A as a white solid.

Example 2-3-24

The compound A (200 mg) obtained in Example 1 was dissolved in butyl acetate (2 ml) with heating under reflux. Heptane (1.5 ml) was added dropwise and the mixture was stirred for 21 hr while allowing to cool. The precipitated solid was collected by filtration and vacuum dried to give crystal form II (158 mg, yield 78%) of compound A as a white solid.

Example 2-3-25

The compound A (200 mg) obtained in Example 1 was dissolved in anisole (2 ml) by heating at 110° C. Heptane (2 ml) was added dropwise and the mixture was stirred for 21 hr while allowing to cool. The precipitated solid was collected by filtration and vacuum dried to give crystal form II (187 mg, yield 89%) of compound A as a white solid.

Example 2-3-26

The compound A (200 mg) obtained in Example 1 was dissolved in butyl acetate (2 ml) with heating under reflux. After rapid cooling, the mixture was stirred for 2 hr. The precipitated solid was collected by filtration and vacuum dried to give crystal form II (131 mg, yield 66%) of compound A as a white solid.

Example 2-4

Production of Crystal Form II of the Compound A

Step 1

1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester (48 g, 86 mmol) obtained in Example 1, Step 5 was dissolved in methanol (300 ml), water (5 ml) and 28% sodium methoxide methanol solution (176 ml, 862 mmol) were added, and the mixture was heated under reflux for 24 hr. The reaction mixture was allowed to cool to room temperature, neutralized with 6N hydrochloric acid and methanol was evaporated under reduced pressure. Water was added to the obtained solution and, after stirring, the precipitated solid was collected by filtration. The obtained solid was dissolved in ethyl acetate, washed with water, and dried over sodium sulfate. The mixture was filtered and the filtrate was concentrated under reduced pressure. The obtained residue was recrystallized from ethyl acetate-hexane to give compound A (primary crystal 29.5 g, secondary crystal 2.8 g, in total 32.3 g, yield 86%) as a white solid.

m.p. 151-152° C.

$^1$H NMR (DMSO-$d_6$ 300 MHz) (δ) ppm: 0.72 (3H, d, J=60.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H,s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Step 2

Compound A (32.3 g) obtained in Step 1 was dissolved in butyl acetate (160 ml) with heating under reflux. The crystal form II of Example 2 was seeded at 63° C. and the mixture was stirred for 3 hr while allowing to cool. The precipitated solid was collected by filtration and vacuum dried to give the crystal of compound A (crystal form II) (24.79 g, yield 77%) as a white solid.

Example 2-5

Production of Crystal Form II of the Compound A

Step 1

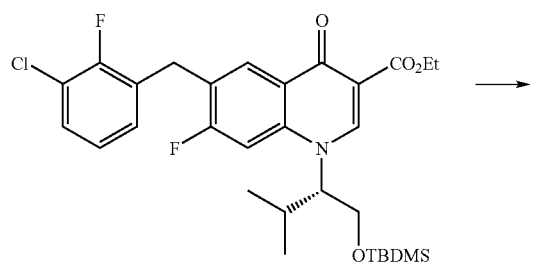

1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester (19 g, 33 mmol) obtained in Example 1, Step 5 was dissolved in isopropanol (100 ml), 1N aqueous sodium hydroxide solution (200 ml, 200 mmol) was added, and the mixture was heated under reflux for 2.5 hr. The reaction mixture was allowed to cool to room temperature, and the mixture was filtered through Celite. The filtrate was acidified by adding concentrated hydrochloric acid, and stirred at room temperature for 2 hr. The precipitated solid was collected by filtration and vacuum dried to give 6-(3-chloro-2-fluorobenzyl)-7-fluoro-1-((S)-1-hydroxymethyl-2-methylpropyl)-4-oxo-1,4-dihydroquinoline-3-carboxylic acid (12 g, yield 82%) as a pale-yellow solid.

$^1$H NMR (DMSO-$d_6$ 400 MHz) (δ) ppm: 0.71 (3H, d, J=6.5 Hz), 1.13 (3H, d, J=6.5 Hz), 2.36 (1H, br), 3.77 (1H, br), 3.94 (1H, br), 4.25 (2H, s), 4.77 (1H, br), 5.16 (1H, t, J=2.4 Hz), 7.19-7.23 (1H, m), 7.32-7.35 (1H, m), 7.48-7.52 (1H, m), 8.24-8.28 (2H, m), 9.00 (1H, s), 15.00 (1H, s)

Step 2

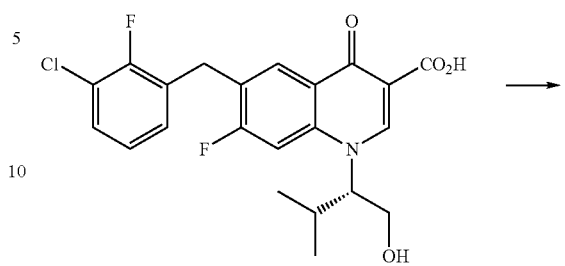

The compound (12 g, 27 mmol) obtained in Step 1 was dissolved in methanol (64 ml), 28% sodium methoxide methanol solution (52 ml, 256 mmol) was added, and the mixture was heated under reflux for 24 hr. The reaction mixture was allowed to cool to room temperature and filtered through Celite. The filtrate was concentrated under reduced pressure. The residue was acidified by adding water (360 ml) and concentrated hydrochloric acid, and extracted with ethyl acetate. The organic layer was washed successively with water and saturated brine and dried over sodium sulfate. The mixture was filtered, and the filtrate was concentrated under reduced pressure to give a crude product (13 g) as a brown oil. The obtained crude product (13 g) was dissolved in isobutyl acetate (60 ml) by heating and, after seeding, the mixture was stirred for 23 hr while allowing to cool. The precipitated solid was collected by filtration, and vacuum dried to give compound A (9.2 g, yield 75%) as a white solid.

$^1$H NMR (DMSO-$d_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H,s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Step 3

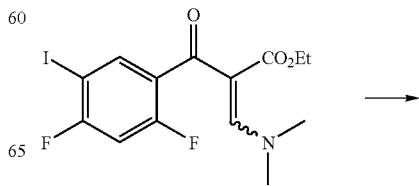

-continued

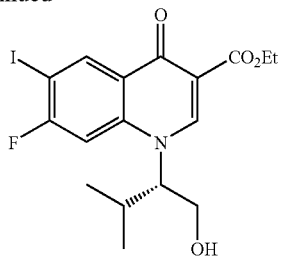

2-(2,4-Difluoro-5-iodobenzoyl)-3-dimethylaminoacrylic acid ethyl ester (20 g) obtained in Example 1, Step 2 was subject to slurry washing with a mixed solvent of ethyl acetate (60 ml) and hexane (40 ml) and heated under reflux. The mixture was filtered, and the remaining solid was vacuum dried to give 7-fluoro-1-((S)-1-hydroxymethyl-2-methylpropyl)-6-iodo-4-oxo-1,4-dihydroquinoline-3-carboxylic acid ethyl ester (18 g, yield 94%) as a beige solid.

$^1$H NMR (DMSO-d$_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS(ESI): M+448

Step 4

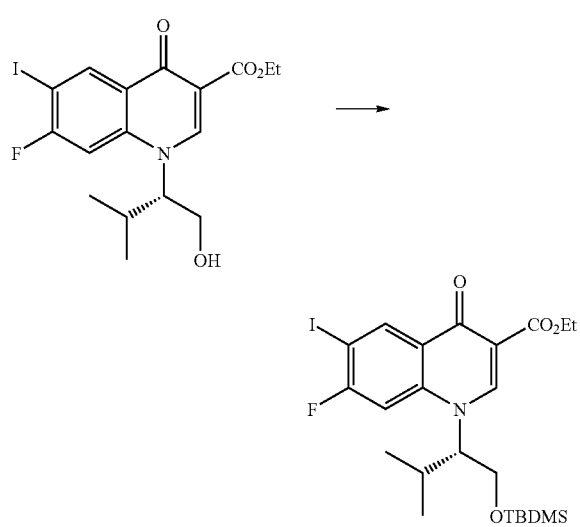

The compound (19 g, 42 mmol) obtained in Step 3 was dissolved in dimethylformamide (65 ml), imidazole (3.4 g, 49.9 mmol) and tert-butyldimethylsilyl chloride (7.2 g, 47.8 mmol) were added, and the mixture was stirred at room temperature for 1.5 hr. Water was added to the reaction mixture, and the mixture was extracted with ethyl acetate. The organic layer was washed successively with water, saturated aqueous ammonium chloride solution and saturated brine, and dried over sodium sulfate. The organic layer was filtered, and the filtrate was concentrated under reduced pressure to give a crude product (24 g) of 1-((S)-1-tert-butyldimethylsilyloxymethyl-2-methylpropyl)-7-fluoro-6-iodo-4-oxo-1,4-dihydroquinoline-3-carboxylic acid ethyl ester as a beige amorphous form.

$^1$H NMR (CDCl$_3$ 400 MHz) (δ) ppm: −0.07 (3H, s), −0.05 (3H, s), 0.77 (9H, s), 0.84 (3H, d, J=6.5 Hz), 1.18 (3H, d, J=6.5 Hz), 1.40 (3H, t, J=7.2 Hz), 2.35-2.50 (1H, m), 3.85-3.95 (1H, m), 3.98-4.10 (2H, m), 4.30-4.40 (2H, m), 7.26 (1H,s), 8.64 (1H, s), 8.94 (1H, d, J=7.2 Hz)

MS(ESI): M+562

Step 5

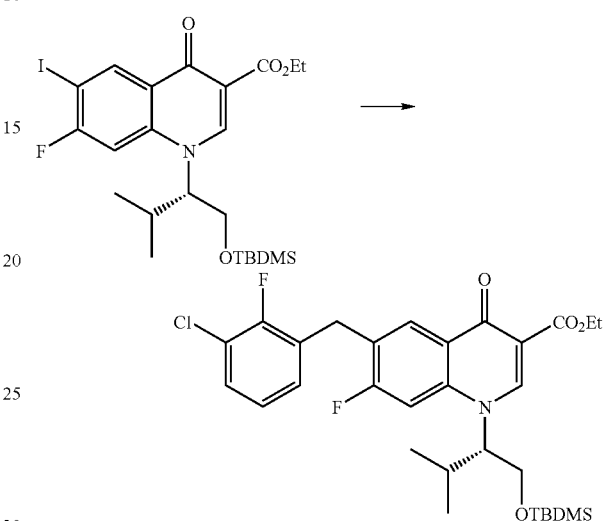

The crude product (24 g) obtained in Step 4 was dissolved in tetrahydrofuran (200 ml) and, under an argon stream, dibenzylideneacetonepalladium(II) (984 mg, 1.7 mmol) and trifurylphosphine (795 mg, 3.4 mmol) were added, and a solution (56 ml, 56 mmol) of 1M 3-chloro-2-fluorobenzylzinc bromide obtained in the same manner as in Example 1, Step 5 in tetrahydrofuran was added dropwise at 60° C. After the completion of the dropwise addition, the mixture was stirred with heating at the same temperature for 2 hr. The reaction mixture was allowed to cool to room temperature, saturated aqueous ammonium chloride solution was added, and filtered through Celite, and the filtrate was extracted twice with ethyl acetate. The organic layer was washed successively with water (twice) and saturated brine, and dried over magnesium sulfate. The organic layer was filtered, and the filtrate was concentrated under reduced pressure to give a crude product (30 g) of 1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester as a brown paste.

Step 6

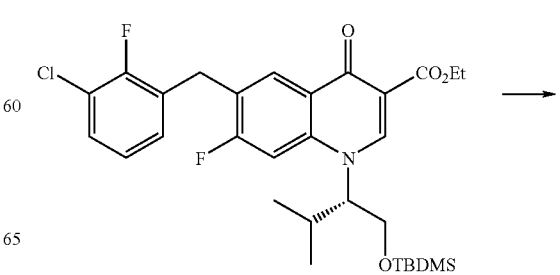

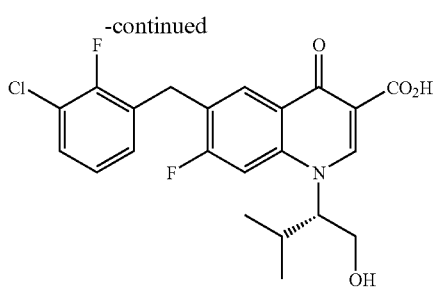

The crude product (30 g) obtained in Step 5 was dissolved in isopropanol (150 ml), 1N aqueous sodium hydroxide solution (300 ml, 300 mmol) was added, and the mixture was heated under reflux for 2.5 hr. The reaction mixture was allowed to cool to room temperature, and the mixture was filtered through Celite. The filtrate was acidified by adding concentrated hydrochloric acid, and the mixture was stirred at room temperature for 2 hr. The precipitated solid was collected by filtration and vacuum dried to give a crude product (18 g) as a beige solid. The obtained crude product (18 g) was suspended in butyl acetate (90 ml), and subjected to slurry stirring with heating under reflux for 1 hr. The suspension was allowed to cool to room temperature, filtered and vacuum dried to give 6-(3-chloro-2-fluorobenzyl)-7-fluoro-1-((S)-1-hydroxymethyl-2-methylpropyl)-4-oxo-1,4-dihydroquinoline-3-carboxylic acid (11 g, yield 62% (relative to Step 3)) as a white solid.

$^1$H NMR (DMSO-$d_6$ 400 MHz) (δ) ppm: 0.71 (3H, d, J=6.5 Hz), 1.13 (3H, d, J=6.5 Hz), 2.36 (1H, br), 3.77 (1H, br), 3.94 (1H, br), 4.25 (2H, s), 4.77 (1H, br), 5.16 (1H, t, J=2.4 Hz), 7.19-7.23 (1H, m), 7.32-7.35 (1H, m), 7.48-7.52 (1H, m), 8.24-8.28 (2H, m), 9.00 (1H, s), 15.00 (1H, s)

MS(ESI): M+436

Step 7

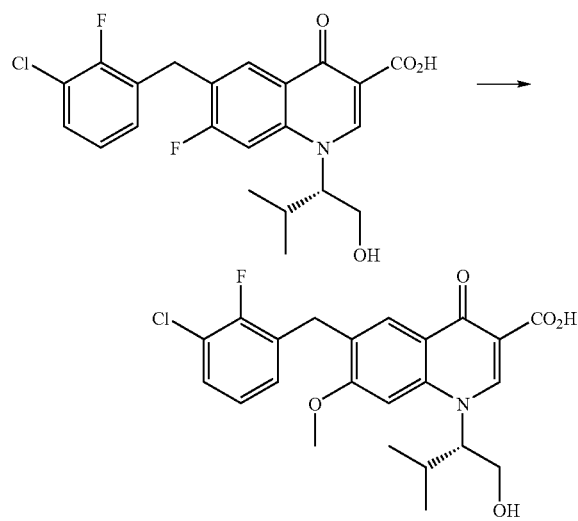

The compound (11 g, 26 mmol) obtained in Step 6 was dissolved in methanol (60 ml), 28% sodium methoxide methanol solution (52 ml, 256 mmol) was added, and the mixture was heated under reflux for 24 hr. The reaction mixture was allowed to cool to room temperature and filtered through Celite, and the filtrate was concentrated under reduced pressure. The residue was acidified by adding water (330 ml) and concentrated hydrochloric acid, and the mixture was extracted with ethyl acetate. The organic layer was washed successively with water and saturated brine, and dried over sodium sulfate. The mixture was filtered, and the filtrate was concentrated under reduced pressure to give a crude product (12 g) as a brown oil. The obtained crude product (12 g) was dissolved in isobutyl acetate (60 ml) by heating under reflux. A seed crystal (crystal form II of compound A) was seeded, and the mixture was stirred for 23 hr while allowing to cool. The precipitated solid was collected by filtration and vacuum dried to give compound A (8.2 g, yield 71%) as a white solid.

$^1$H NMR (DMSO-$d_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H,s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+448

Step 8

Compound A (7.66 g) obtained in Step 7 and compound A (9.17 g) obtained in Step 2 were dissolved in isobutyl acetate (84 ml) by heating under reflux and the mixture was stirred for 16 hr while allowing to cool. The precipitated solid was collected by filtration and vacuum dried to give crystal form II (14.73 g, yield 88%) of compound A as a white solid.

Example 2-6

Production of Crystal Form II of the Compound A

Step 1

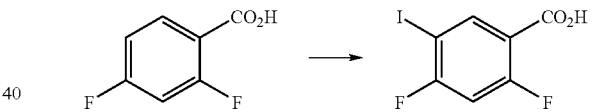

2,4-Difluorobenzoic acid (100 g, 633 mmol) was dissolved in trifluoromethanesulfonic acid (400 ml) and N-iodosuccinimide (157 g, 696 mmol) was added by portions at not more than 5° C. After the completion of the addition, the mixture was stirred at 50° C. for 1.5 hr. The reaction mixture was poured into iced water, and the mixture was stirred for 1 hr. The precipitated solid was collected by filtration, washed successively with water and hexane, and vacuum dried to give 2,4-difluoro-5-iodobenzoic acid (179 g yield quantitative) as a white solid.

$^1$H NMR (CDCl$_3$ 300 MHz) (σ) ppm: 6.94 (1H, dd, J=10.3, 10.3 Hz), 8.46 (1H, d, J=7.5 Hz)

Step 2

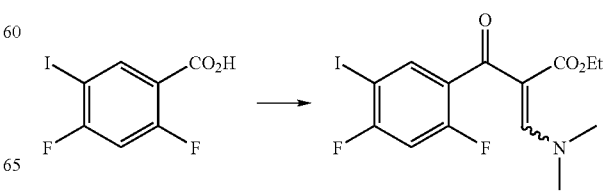

The compound (28 g, 100 mmol) obtained in Step 1 was dissolved in ethyl acetate (300 ml), oxalyl chloride (11 ml, 122 mmol) and dimethylformamide (catalytic amount) were added, and the mixture was stirred at room temperature for 2 hr. The filtrate was concentrated under reduced pressure and azeotroped with toluene. The residue was dissolved in tetrahydrofuran (100 ml), this solution was added dropwise to a solution of ethyl 3,3-dimethylaminoacrylate (17 g, 120 mmol) and triethylamine (21 ml, 150 mmol) in tetrahydrofuran (100 ml), and the mixture was heated under reflux for 3 hr. The reaction mixture was allowed to cool and ethyl acetate (200 ml) was added. The mixture was washed successively with water (twice) and saturated brine, and dried over sodium sulfate. The mixture was filtered and the filtrate was concentrated under reduced pressure. The obtained residue was subject to slurry stirring with a mixed solvent of diethyl ether (50 ml) and hexane (50 ml). The mixture was filtered and the remaining solid was vacuum dried to give a crude product (26 g, yield 63%) of 2-(2,4-difluoro-5-iodobenzoyl)-3-dimethylaminoacrylic acid ethyl ester as a yellow solid.

Step 3

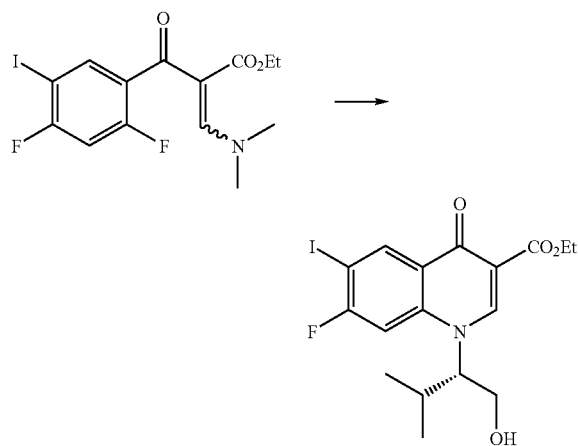

The crude product (22 g, 55 mmol) obtained in Step 2 was dissolved in tetrahydrofuran (110 ml), (S)-(+)-valinol (6.8 g, 65.8 mmol) was added, and the mixture was stirred with heating at 50° C. for 30 min. The reaction mixture was concentrated under reduced pressure, and the residue was dissolved in ethyl acetate (100 ml), washed successively with water and saturated brine, and dried over magnesium sulfate. The mixture was filtered and the filtrate was concentrated under reduced pressure. The obtained residue was dissolved in dimethylformamide (80 ml), potassium carbonate (19 g, 137 mmol) was added, and the mixture was stirred with heating at 60° C. for 1.5 hr. The reaction mixture was allowed to cool to room temperature and concentrated under reduced pressure. Water (250 ml) was added to the obtained residue and the mixture was stirred at room temperature for 30 min. The precipitated solid was collected by filtration. The obtained solid was washed successively with a mixed solvent of water (100 ml), ethyl acetate (10 ml) and hexane (40 ml) and vacuum dried to give 7-fluoro-1-((S)-1-hydroxymethyl-2-methylpropyl)-6-iodo-4-oxo-1,4-dihydroquinoline-3-carboxylic acid ethyl ester (22 g, yield 88%) as a pale-yellow solid.

$^1$H NMR (DMSO-$d_6$ 300 MHz) (δ) ppm: 0.72 (3H, d, J=6.6 Hz), 1.10 (3H, d, J=6.6 Hz), 1.28 (3H, t, J=7.0 Hz), 2.27 (1H, br), 3.77 (1H, br), 3.86 (1H, br), 4.23 (2H, q, J=7.0 Hz), 4.56 (1H, br), 5.12 (1H, t, J=4.9 Hz), 8.09 (1H, d, J=11.1 Hz), 8.62 (1H, d, J=7.5 Hz), 8.68 (1H, s)

MS(ESI): M+448

Step 4

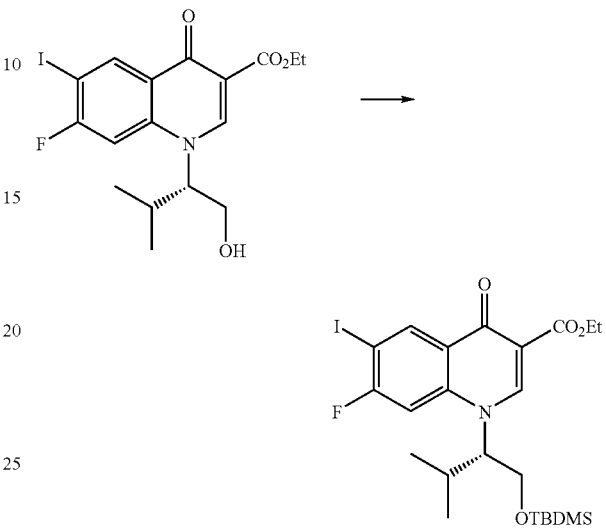

The compound (22 g, 48 mmol) obtained in Step 3 was dissolved in dimethylformamide (60 ml), imidazole (3.9 g, 57.7 mmol) and tert-butyldimethylsilyl chloride (8.0 g, 53.0 mmol) were added, and the mixture was stirred at room temperature for 1.5 hr. The reaction mixture was concentrated under reduced pressure, and the obtained residue was dissolved in ethyl acetate (200 ml), washed successively with water (twice) and saturated brine, and dried over sodium sulfate. The mixture was filtered and the filtrate was concentrated under reduced pressure. The obtained residue was purified by silica gel chromatography (ethyl acetate:hexane=3:7 to 4:6) to give 1-((S)-1-tert-butyldimethylsilyloxymethyl-2-methylpropyl)-7-fluoro-6-iodo-4-oxo-1,4-dihydroquinoline-3-carboxylic acid ethyl ester (25 g, yield 92%) as a white wax.

$^1$H NMR (CDCl$_3$ 400 MHz) (δ) ppm: −0.07 (3H, s), −0.05 (3H, s), 0.77 (9H, s), 0.84 (3H, d, J=6.5 Hz), 1.18 (3H, d, J=6.5 Hz), 1.40 (3H, t, J=7.2 Hz), 2.35-2.50 (1H, m), 3.85-3.95 (1H, m), 3.98-4.10 (2H, m), 4.30-4.40 (2H, m), 7.26 (1H,s), 8.64 (1H, s), 8.94 (1H, d, J=7.2 Hz)

MS(ESI): M+562

Step 5

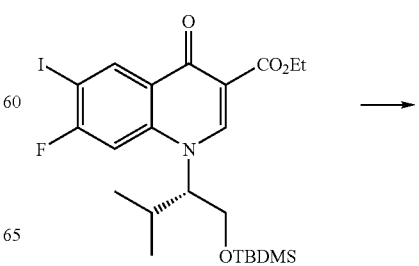

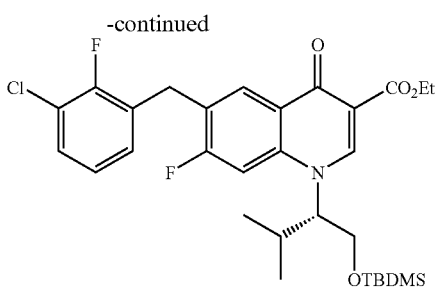

The compound (25 g, 44 mmol) obtained in Step 4 was dissolved in tetrahydrofuran (200 ml) and, under an argon stream, dibenzylideneacetonepalladium(II) (1.0 g, 1.8 mmol) and trifurylphosphine (824 mg, 3.5 mmol) were added. A solution (58 ml, 58 mmol) of 1M 3-chloro-2-fluorobenzylzinc bromide obtained in the same manner as in Example 1, Step 5 in tetrahydrofuran was added dropwise at 60° C. After the completion of the dropwise addition, the mixture was heated under reflux for 3 hr. The reaction mixture was allowed to cool to room temperature, ethyl acetate (200 ml) was added, washed successively with 1N hydrochloric acid, water, saturated aqueous sodium hydrogen carbonate, water and saturated brine, and dried over sodium sulfate. The mixture was filtered and the filtrate was concentrated under reduced pressure. The obtained residue was purified by silica gel chromatography (ethyl acetate:hexane=4:6 to 1:1) to give 1-((S)-1-tert-butyldimethylsilyloxymethyl-2-methylpropyl)-6-(3-chloro-2-fluorobenzyl)-7-fluoro-4-oxo-1,4-dihydroquinoline-3-carboxylic acid ethyl ester (17 g, yield 68%) as a pale-yellow oil.

$^1$H NMR (CDCl$_3$ 400 MHz) (δ) ppm: −0.09 (3H, s), −0.05 (3H, s), 0.75 (9H, s), 0.85 (3H, d, J=6.7 Hz), 1.18 (3H, d, 6.7 Hz), 1.39 (3H, t, J=7.1 Hz), 2.45 (1H, br), 3.89-3.92 (1H, m), 3.98-4.02 (1H, m), 4.07-4.12 (1H, m), 4.12 (2H, s), 4.34-4.41 (2H, m), 6.96-7.00 (1H, m), 7.03-7.05 (1H, m), 7.21-7.24 (1H, m), 7.26-7.29 (1H, m), 8.39 (1H, d, J=8.8 Hz), 8.63 (1H, s)

Step 6

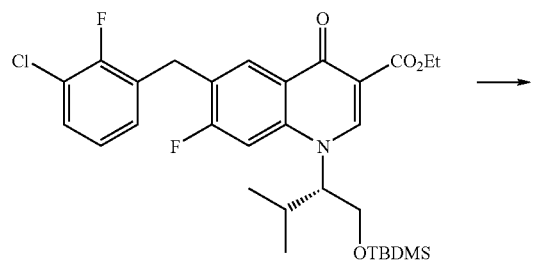

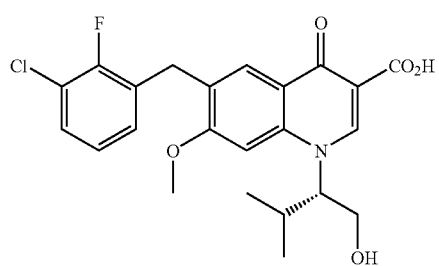

The compound (17 g, 30 mmol) obtained in Step 5 was dissolved in methanol (120 ml), 28% sodium methoxide methanol solution (62 ml, 304 mmol) was added, and the mixture was heated under reflux for 19 hr. The reaction mixture was allowed to cool to room temperature, water (200 ml) was added, and methanol was evaporated under reduced pressure. The residue was acidified by adding concentrated hydrochloric acid, extracted with ethyl acetate, and dried over sodium sulfate. The mixture was filtered, and the filtrate was concentrated under reduced pressure to give a crude product (14 g) of compound A as a pale-yellow oil.

Step 7

Compound A (14.11 g) obtained in Step 6 was suspended in a mixed solvent of ethyl acetate (20 ml) and hexane (20 ml) at room temperature, a seed crystal (crystal form II of compound A) was seeded, and the mixture was stirred for 1 hr. The suspension was filtered, and the remaining solid was vacuum dried to give compound A (crystal form II, 10.40 g, yield 77%) as a white solid.

Example 3

Production of Crystal Form III of the Compound A

Example 3-1

Production of Crystal Form III of the Compound A

The crystal form II of compound A (10.0 g, 22.3 mmol) obtained in Example 2-2 was added to isobutyl acetate (30 mL) and the crystal was dissolved by heating under reflux. The solution was cooled to 90° C., and stirred for 5 hr to allow precipitation of crystals. This solution was further allowed to cool to room temperature, and further stirred for 12 hr. The precipitated crystal was collected by filtration. The obtained crystal was washed with isobutyl acetate (10 mL) and vacuum dried to give a white crystal (9.85 g, yield 98.5%). Since this crystal was confirmed to be different from crystal form II by XRPD analysis, a crystal showing the XRPD chart (FIG. 1) as this crystal was taken as crystal form III.

Example 3-2

Production of Crystal Form III of the Compound A

The crystal form II of compound A (250 g, 558 mmol) obtained in Example 2-2 was added to isobutyl acetate (750 mL). A seed crystal (12.5 g) of the crystal form III of compound A obtained in Example 3 was added at room temperature and the mixture was stirred for 17 hr. The precipitated crystal was collected by filtration. The obtained crystal was washed with isobutyl acetate (250 mL), and vacuum dried to give the object product (crystal form III, 259 g, yield 98.6%) as a white crystal. This crystal was confirmed to be equivalent to the standard product of the crystal (crystal form III of compound A obtained in Example 3-1) by XRPD analysis.

Example 3-3

Production of Crystal Form III of the Compound A

Compound A (crystal form II, 10.0 g, 22.3 mmol) obtained in Example 2-2 was added to isopropanol (30 mL), and the mixture was heated under reflux to dissolve the crystal. The solution was cooled to 70° C., a seed crystal (10 mg) of the crystal form III of compound A obtained in Example 3-1 was added, and the mixture was stirred for 5 hr. This mixture was further allowed to cool to room temperature, stirred for 12 hr, and the crystal was collected by filtration. The obtained crystal was washed with isopropanol (10 mL), and vacuum dried to give the object product (crystal form III, 9.72 g, yield 97.2%) as a white crystal. This crystal was confirmed to be equivalent to the standard product of the crystal (crystal form III of compound A obtained in Example 3-1) by XRPD analysis.

Example 3-4

Production of Crystal Form III of Compound A

The crystal form II of compound A (7.00 g, 15.6 mmol) obtained in Example 2-2 was added to a mixed solution of ethanol (52.5 mL) and water (7 mL) and dissolved by heating. Water (28 mL) was added, a seed crystal (10 mg) of the object product was added at 70° C. and the mixture was stirred for 4 hrs. After allowing to cool to room temperature, the mixture was ice-cooled and further stirred for 2 hrs, and the crystals were collected by filtration. The obtained crystals were washed with a mixed solution of cool ethanol (8.4 mL) and water (5.6 mL) and vacuum dried to give the object product as white crystals (crystal form III, 6.77 g, yield 96.8%). This crystal was confirmed to be equivalent to the standard product (Example 3-1) by XRPD analysis.

Experimental Example

The property values of each crystal form were determined by the following analysis tests, and the stability test of each crystal form was performed using them as indices.

Sample

Unless otherwise specified, the aforementioned crystal (crystal form I) obtained in Reference Example 1, the crystal (crystal form II) obtained in Example 1 and the crystal (crystal form III) obtained in Example 3-1 were used as samples.

Analysis Test

1. X-ray Powder Diffractometry

This test aims at obtaining X-ray powder diffraction patterns to specify the crystal form of the crystals obtained in Reference Example 1, Example 1 and Example 3-1. The diffraction patterns are utilized to specify the crystal form, evaluate the stability, to determine the purity and the like.

A sample was fixed to an aluminum cell, and the measurement was performed using an X-ray powder diffractometer (RINT 2000/PC Ultima+, manufactured by Rigaku Corporation, X-ray source: Cu—Kα1 ray, tube voltage: 40 kV, tube electric current: 40 mA, scan speed: 5° per min, step width: 0.02°, diffraction angle: 5-40°), based on which the diffraction patterns were obtained. The obtained diffraction patterns are shown in FIG. 1.

As shown in FIG. 1, X-ray powder diffraction patterns obtained from respective samples were different.

Therefore it was confirmed that the crystals obtained in Reference Example 1, Example 1 and Example 3-1 were distinct from each other, and show characteristic diffraction patterns as shown in the X-ray powder diffraction pattern. Therefore, in the present specification, they were named as crystal form I, crystal form II and crystal form III, based on these X-ray powder diffraction patterns.

For specification of the crystal form, the diffraction peak characteristic of each crystal may be evaluated in a comprehensive manner based on the diffraction chart in FIG. 1.

The main diffraction peaks and characteristic diffraction peaks specified from the diffraction patterns in FIG. 1 are shown below.

Crystal Form I

Main diffraction peak: 2θ=6.58, 14.40, 14.64, 15.24, 16.48, 19.16, 20.90, 21.14, 22.24, 24.74, 25.64, 26.12, 27.20°;

Characteristic diffraction peak: 2θ=6.58, 14.40, 19.16, 20.90, 21.14°.

Crystal Form II

Main diffraction peak: 2θ=6.56, 9.04, 13.20, 14.62, 15.24, 16.48, 19.86, 20.84, 21.22, 22.24, 25.22, 25.96, 26.12, 27.34°;

Characteristic diffraction peak: 2θ=6.56, 13.20, 19.86, 20.84, 21.22, 25.22°.

Crystal Form III

Main diffraction peak: 2θ=8.54, 14.02, 15.68, 15.90, 16.00, 17.06, 17.24, 17.84, 18.12, 19.50, 19.90, 22.26, 22.68, 23.02, 24.16, 24.76, 25.18, 25.74, 25.98, 27.50, 28.80, 30.38, 30.72, 32.54°;

Characteristic diffraction peak: 2θ=8.54, 14.02, 15.68, 17.06, 17.24, 24.16, 25.74°.

2. Thermal Analysis

This test aims at the measurement of the enthalpy and extrapolated onset temperature at an endothermic peak on the Differential Scanning Calorimetry (DSC) measurement curve. These values are among the indices of the stability of the above-mentioned crystal form I, crystal form II and crystal form III, and can be used as an index to specify the crystal form.

2.1. Enthalpy and extrapolated onset temperature of crystal form I and crystal form II CCrystal form I and crystal form II were subjected to measurement using a Differential Scanning Calorimetry (DSC) measurement apparatus (DSC8240, manufactured by Rigaku Corporation), under atmosphere, measurement sample 5±1 mg, temperature rise rate: 10° C./min, aluminum open pan, and alumina oxide as a reference. The enthalpy and extrapolated onset temperature at an endothermic peak on the obtained DSC curve were determined.

2.2. Enthalpy and extrapolated onset temperature of crystal form III

Crystal form III was subjected to measurement using a DSC measurement apparatus (DSC8240, manufactured by Rigaku Corporation), under atmosphere, measurement sample 5.0±0.5 mg, temperature rise rate: 5° C./min, aluminum closed pan, and alumina oxide as a reference. The enthalpy and extrapolated onset temperature at an endothermic peak on the obtained DSC curve were determined.

The results are shown in Table 1.

TABLE 1

| DSC curve at endothermic peak on enthalpy and extrapolated onset temperature | | |
|---|---|---|
| | Endothermic peak | |
| Crystal form | Enthalpy (J/g) | Extrapolated onset temperature (° C.) |
| Crystal form I | 51.080 | 150.3 |
| Crystal form II | 53.542 | 151.2 |
| Crystal form III | 81.404 | 162.1 |

As shown in Table 1, crystal form III shows greatest enthalpy and highest extrapolated onset temperature among three crystal forms crystal form I. Thus, crystal form III was confirmed to be most stable form.

3. Purity Test

This test aims at measurement of the purity of compound A. The purity can be used as indices of chemical stability.

3.1. Purity of compound of crystal form I and crystal form II

Each sample (crystal form I and crystal form II, ca. 10 mg) was dissolved in acetonitrile to make an amount of 10 mL and used as a sample solution. This solution (10 μL) was applied to high performance liquid chromatography (HPLC) under the following conditions. The peak area of each sample solution was measured by automatic integration, and the purity was determined by the following formula. The purity is shown in the Tables 5 and 6 below.

Purity (%)=100−($A_{sum}/A_s$)×100

As: total peak area of peaks obtained from sample solution

Asum: total peak area of peaks other than the main peak obtained from sample solution Test Conditions Detector: UV absorptiometer (wavelength: 259 nm)

Column: CAPCELL PAK MG (inner diameter 4.6 cm, length 15 cm, particle size 5 μm, manufactured by Shiseido Co., Ltd.

Column temperature: constant temperature around 40° C.

Mobile phase A: trifluoroacetic acid solution (1:1000)

Mobile phase B: solution of trifluoroacetic acid in acetonitrile (1:1000)

Gradient program: As shown in the following Table 2, the mixing ratio of mobile phase A and mobile phase B is changed to control concentration gradient.

TABLE 2

| Time (min) after injection | Mobile phase A (%) | Mobile phase B (%) |
|---|---|---|
| 0 | 55 | 45 |
| 0-5 | 55→52 | 45→48 |
| 5-15 | 52 | 48 |
| 15-25 | 52→20 | 48→80 |
| 25-35 | 20 | 80 |
| 35-36 | 20→55 | 80→45 |
| 36-45 | 55 | 45 |

Flow rate: 1 mL/min 3.2. Purity of compound of crystal form III

A sample (crystal form III, ca. 50 mg) was dissolved in a mixture (4:1) of mobile phase B and mobile phase A to make an amount of 50 mL, which was used as a sample solution. This solution (1 mL) was precisely measured and a mixture (4:1) of mobile phase B and mobile phase A was added to precisely make an amount of 100 mL, which was used as a standard solution. The sample solution and standard solution (15 μL) was applied to high performance liquid chromatography (HPLC) under the following conditions. The peak area of each solution was measured by automatic integration, and the purity was determined by the following formula. The purity is shown in the Table 7 below.

Purity (%)=100−($A_{sum}/A_r$)

$A_r$: peak area of main peak obtained from standard solution $A_{sum}$: total peak area of peaks other than the main peak obtained from sample solution Test Conditions Detector: UV absorptiometer (wavelength: 259 nm)

Column: Waters XTerra MC C18 (inner diameter 4.6 cm, length 5 cm, particles diameter 2.5 μm, manufactured by Waters)

Column temperature: constant temperature around 40° C.

Mobile phase A: phosphoric acid is added to dipotassium hydrogenphosphate solution (1→1149) to adjust pH to 7.0

Mobile phase B: acetonitrile

Gradient program: As shown in the following Table 3, the mixing ratio of mobile phase A and mobile phase B is changed to control concentration gradient.

TABLE 3

| Time (min) after injection | Mobile phase A (%) | Mobile phase B (%) |
|---|---|---|
| 0-15 | 58 | 42 |
| 15-35 | 58→20 | 42→80 |
| 35-45 | 20 | 80 |
| 45-46 | 20→58 | 80→42 |
| 46-55 | 58 | 42 |

Flow rate: 0.9 mL/min

4. Solubility Test

This test aims at measurement of solubility of the crystal in various test solutions and under various pHs. The solubility is one of the indices of the stability of the above-mentioned crystal form I, crystal form II and crystal form III and can be used also as a reference indices of absorbability of crystal form by living organisms.

Each sample (crystal form I type I, crystal form II and crystal form III, ca. 10 mg) was placed in a 10 mL centrifuge tube together with the following test solution (5 mL) and shaken with a shaker (SR-1M; manufactured by Tietech Co., Ltd.) for 14 hours. After shaking, the mixture was centrifuged (3000 rpm, 20 min) and the supernatant was filtered through 0.2 μm pore size—13 mm diameter polytetrafluoroethylene disk filter (Millex-LG; manufactured by Millipore Corporation). The measurement was performed by high performance liquid chromatography (HPLC). The results are shown in Table 4.

TABLE 4

Solubility Test

| | | Solubility (μg/mL) | |
|---|---|---|---|
| Test solution | pH | Crystal form II | Crystal form III |
| Purified water | — | 0.5 | <0.1 |
| Japanese Pharmacopoeia 1st fluid[1] | 1.2 | 0.9 | <0.1 |
| Japanese Pharmacopoeia 2nd fluid[2] | 6.8 | 5.8 | 2.4 |
| McIlvaine[3] | 2.2 | 1.9 | <0.1 |
| | 4 | 0.8 | <0.1 |
| | 5 | 0.4 | <0.1 |
| | 6 | 1.0 | 0.7 |

TABLE 4-continued

Solubility Test

| Test solution | pH | Solubility (μg/mL) | |
|---|---|---|---|
| | | Crystal form II | Crystal form III |
| | 6.8 | 6.3 | 0.7 |
| | 8 | 84 | 23 |

[1] Japanese Pharmacopoeia, General Test Method, Disintegration Test Method, 1st fluid. Hydrochloric acid (7.0 mL) and water are added to sodium chloride (2.0 g) to make an amount of 1000 mL. This solution is transparent and colorless and has a pH of about 1.2.
[2] Japanese Pharmacopoeia, General Test Method, Disintegration Test Method, 2nd fluid. 0.2 mol/L sodium hydroxide sample (118 mL) and water are added to 0.2 mol/L potassium disodium phosphate sample (250 mL) to make an amount of 1000 mL. This solution is transparent and colorless and has a pH of about 6.8.
[3] McIlvaine buffer obtained by mixing disodium hydrogenphosphate and citric acid at a given ratio to adjust to a given pH.

From the above-mentioned results, it was confirmed that crystal form II has higher solubility than crystal form III.

5. Stability Test

A stability test of each sample was performed under the following preservation conditions. The results of crystal form I are shown in Table 5, the results of crystal form II are shown in Table 6, and the results of crystal form III are shown in Table 7.

As shown in Table 6 and Table 7, crystal form II and crystal form III did not show any difference in the test results under all preservation conditions, as compared to the initial sample. In contrast, as shown in Table 5, crystal form I showed changes in the X-ray powder diffraction pattern obtained from sample after preservation under preservation condition# 3 (80° C., preservation in an open container for 3 days) and preservation condition# 5 (60° C., preservation in an open container for 3 weeks), and the X-ray powder diffraction pattern of crystal form I was observed to have overlapped with the X-ray powder diffraction pattern derived from crystal form II. Thus, it was evaluated that a part of the sample showed crystal transition to crystal form II during preservation. The X-ray powder diffraction patterns of the samples preservation sample under preservation conditions# 1-6 of crystal form I are shown in FIG. 2.

TABLE 5

Results of stability test of crystal form I

| | Preservation conditions | Appearance | Purity | XRD | Thermal analysis |
|---|---|---|---|---|---|
| 1 | Initial | — | 99.1% | Diffraction pattern of crystal form I | Endothermic peak (extrapolated onset temperature 150.3° C.) |
| 2 | 80° C. Closed container Preserved for 3 days | No change in appearance | 99.1% | No change in diffraction pattern | No change in DSC curve |
| 3 | 80° C. Open container Preserved for 3 days | No change in appearance | 99.1% | Overlap of diffraction patterns of crystal form I and crystal form II | No change in DSC curve |
| 4 | 60° C. Closed container Preserved for 3 weeks | No change in appearance | 99.1% | No change in diffraction pattern | No change in DSC curve |
| 5 | 60° C. Open container Preserved for 3 weeks | No change in appearance | 99.1% | Overlap of diffraction patterns of crystal form I and crystal form II | No change in DSC curve |
| 6 | 60° C./75% R.H. Open container Preserved for 3 weeks | No change in appearance | 99.1% | No change in diffraction pattern | No change in DSC curve |

R.H.: relative humidity
XRD: X-ray powder diffractometry

TABLE 6

Results of stability test of crystal form II

| | Preservation conditions | Appearance | Purity | XRD | Thermal analysis |
|---|---|---|---|---|---|
| 1 | Initial | — | 98.9% | Diffraction pattern of crystal form II | Endothermic peak (extrapolated onset temperature 151.2° C.) |
| 2 | 80° C. Closed container Preserved for 3 days | No change in appearance | 98.9% | No change in diffraction pattern | No change in DSC curve |
| 3 | 80° C. Open container Preserved for 3 days | No change in appearance | 98.8% | No change in diffraction pattern | No change in DSC curve |
| 4 | 60° C. Closed container Preserved for 3 weeks | No change in appearance | 98.9% | No change in diffraction pattern | No change in DSC curve |
| 5 | 60° C. Open container Preserved for 3 weeks | No change in appearance | 98.8% | No change in diffraction pattern | No change in DSC curve |
| 6 | 60° C./75% R.H. Open container Preserved for 3 weeks | No change in appearance | 98.9% | No change in diffraction pattern | No change in DSC curve |

R.H.: relative humidity
XRD: X-ray powder diffractometry

TABLE 7

Results of stability test of crystal form III

| | Preservation conditions | Appearance | Purity | XRD | Thermal analysis |
|---|---|---|---|---|---|
| 1 | Initial | — | 98.71% | Diffraction pattern of crystal form III | Endothermic peak (extrapolated onset temperature 162.1° C.) |
| 2 | 80° C. Closed container Preserved for 3 days | No change in appearance | 98.68% | No change in diffraction pattern | No change in DSC curve |
| 3 | 80° C. Open container Preserved for 3 days | No change in appearance | 98.69% | No change in diffraction pattern | No change in DSC curve |
| 4 | 60° C. Closed container Preserved for 3 weeks | No change in appearance | 98.67% | No change in diffraction pattern | No change in DSC curve |
| 5 | 60° C. Open container Preserved for 3 weeks | No change in appearance | 98.66% | No change in diffraction pattern | No change in DSC curve |
| 6 | 60° C./75% R.H. Open container Preserved for 3 weeks | No change in appearance | 98.65% | No change in diffraction pattern | No change in DSC curve |

R.H.: relative humidity
XRD: X-ray powder diffractometry

From the results of the above-mentioned stability test, it was observed that the crystal form I was unstable but crystal form II and crystal form III were extremely stable under various preservation conditions. Therefore, it was evidenced that crystal form II and crystal form III are preferable for use as a pharmaceutical product and the like.

As for the absorbability by living organisms, crystal form II is more preferable, and crystal form III is more preferable because it is the most stable crystal.

Since crystal form II and crystal form III are both stable, a mixed crystal of them can be used for the present invention.

Experimental Example

The following explains evaluation methods of the HIV integrase inhibitory activity of a crystal or a mixed crystal of compound A of the present invention.

(i) Construction Of Recombinant Integrase Gene Expression System

The 185th phenylalanine of HIV integrase full length gene (J. Virol., 67, 425-437 (1993)) was substituted by histidine and inserted into the restriction enzyme NdeI and XhoI sites of the plasmid pET21a(+) (manufactured by Novagen), whereby an integrase expression vector pET21a-IN-F185H was constructed.

(ii) Production And Purification Of Integrase Protein

*Escherichia coli* recombinant BL21 (DE3) transformed with plasmid pET21a-IN-F185H obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 3 hr to promote accumulation of the integrase protein. The recombinant *E. coli* was collected in pellets by centrifugal separation and preserved at −80° C.

The *E. coli* was suspended in Lysis buffer (20 mM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (manufactured by Pharmacia Corporation) and stirred at 4° C. for 60 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was applied to a Superdex 75 (Pharmacia Corporation) column for gel filtration. The protein was eluted with Lysis buffer containing 1M sodium chloride.

The obtained fractions of the integrase protein were collected and preserved at −80° C.

(iii) Preparation Of DNA Solution

The following DNA synthesized by Greiner was dissolved in TE buffer (10 mM Tris-hydrochloric acid (pH 8.0), 1 mM EDTA) and mixed with donor DNA, target DNA, and each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and preserved at 25° C. to give a double stranded DNA, which was used for the test.

Donor DNA (− strand having biotin attached to the 5′ terminal)

Donor + strand: 5′-Biotin-ACC CTT TTA GTC AGT GTG GAA AAT CTC TAG CA-3′ (SEQ ID NO:1)

Donor − strand: 5′-ACT GCT AGA GAT TTT CCA CAC TGA CTA AAA G-3′ (SEQ ID NO:2)

Target DNA (+, − strands both having digoxigenin added at 3′ terminal)

Target + strand: 5′-TGA CCA AGG CTA ATA TCA CT-Dig-3′ (SEQ ID NO:3)

Target − strand: 5′-AGT GAA TTA GCC CTT GGT CA-Dig-3′ (SEQ ID NO:4)

(iv) Determination Of Enzyme (Hiv Integrase) Inhibitory Activity

The donor DNA was diluted with TE buffer to 10 nM, of which 50 μl was added to each well of streptavidin-coated microtiter plate (manufactured by Roche) and allowed to adsorb at 37° C. for 60 min. The DNA was then washed with phosphate buffer (Dulbecco PBS, Sanko Junyaku Co., Ltd.) containing 0.1% Tween 20 and phosphate buffer. Then, a reaction mixture (70 μl, see the following * for the composition), a test substance (10 μl) diluted with the reaction mixture and 100 μg/ml integrase protein (10 μl) were added to each well and reacted at 37° C. for 60 min.

Then, 50 nM target DNA (10 μl) was added, reacted at 37° C. for 10 min and washed with phosphate buffer containing 0.1% Tween 20 to stop the reaction.

Then, 100 mU/ml peroxidase labeled anti-digoxigenin antibody solution (manufactured by Roche, 100 μl) was added, and the mixture was reacted at 37° C. for 60 min, followed by washing with phosphate buffer containing 0.1% Tween 20.

A peroxidase color solution (manufactured by Bio Rad, 100 μl) was added and allowed to react at room temperature for 4 min. The color reaction was stopped by adding 1N sulfuric acid (100 μl). The absorbance at 450 nm was measured.

The HIV integrase inhibitory activity ($IC_{50}$) of the compound A of the present invention was calculated from the inhibition rate according to the following formula. The results are shown in Table 8.

Inhibition rate (%)=[1−(Object−Blank)/(Control−Blank)]×100

Object; absorbance of well in the presence of test compound

Control; absorbance of well in the absence of test compound

Blank; absorbance of well in the absence of test compound, in the absence of integrase protein

*Composition of the reaction mixture: 30 mM morpholinopropanesulfonic acid (MOPS), 5 mM $MgCl_2$, 3 mM dithiothreithol (DTT), 0.1 mg/mL bovine serum albumin (BSA), 5% glycerol, 10% dimethyl sulfoxide (DMSO), 0.01% Tween 20

TABLE 8

| Compound No. | Enzyme activity $IC_{50}$ (μM) |
| --- | --- |
| Compound A | 0.0029 |

Evaluation Of Antivirus Activity

The effect of combined use of a crystal or a mixed crystal of compound A of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and a crystal or a mixed crystal of compound A and the like are evaluated by XTT method using CEM-SS cells infected with HIV-1 IIIB.

In addition, the effect of combined use of three agents of a crystal or a mixed crystal of compound A, zidovudine and lamivudine, or a crystal or a mixed crystal of compound A, tenofovir and lamivudine, and the like is evaluated.

Prior to the combined use test, $IC_{50}$ and $CC_{50}$ of each pharmaceutical agent alone are measured. 5 concentrations of pharmaceutical agent a and 9 concentrations of pharmaceutical agent b, determined based on these results, are combined to evaluate the effect of combined use of two agents. For combined use of three agents, a high concentration pharmaceutical agent b and a pharmaceutical agent c are mixed and pharmaceutical agent a and the concentration are combined for evaluation.

The test results of the crystal or mixed crystal of compound A and combination drug alone or in combination thereof are analyzed based on the programs of Prichard and Shipman MacSynergy II version 2.01 and Deltagraph version 1.5d.

A three-dimensional plot is drawn from % inhibition at the concentrations of each combined pharmaceutical agent, obtained from 3 times of tests, with 95% (or 68%, 99%) confidence limits, and the effect of the combined use is evaluated based on the numerical values of $μM^2$% calculated therefrom. The criteria of evaluation are shown in the following.

| Definition of interaction | $μM^2$ % |
| --- | --- |
| Strong synergistic action | >100 |
| Slight synergistic action | +52−+100 |
| Additive action | +50−−50 |
| Slight antagonistic action | −51−−100 |
| Strong antagonistic action | <−100 |

INDUSTRIAL FIELD OF UTILIZATION

The crystal of compound A of the present invention, which has the above-mentioned particular crystal form, shows an anti-HIV effect as well as superior crystal stability. Therefore, it is useful as a starting material of a pharmaceutical composition, particularly, various pharmaceutical compositions for the prophylaxis and/or treatment of AIDS.

SEQUENCE LISTING FREE TEXT

Figure 1:
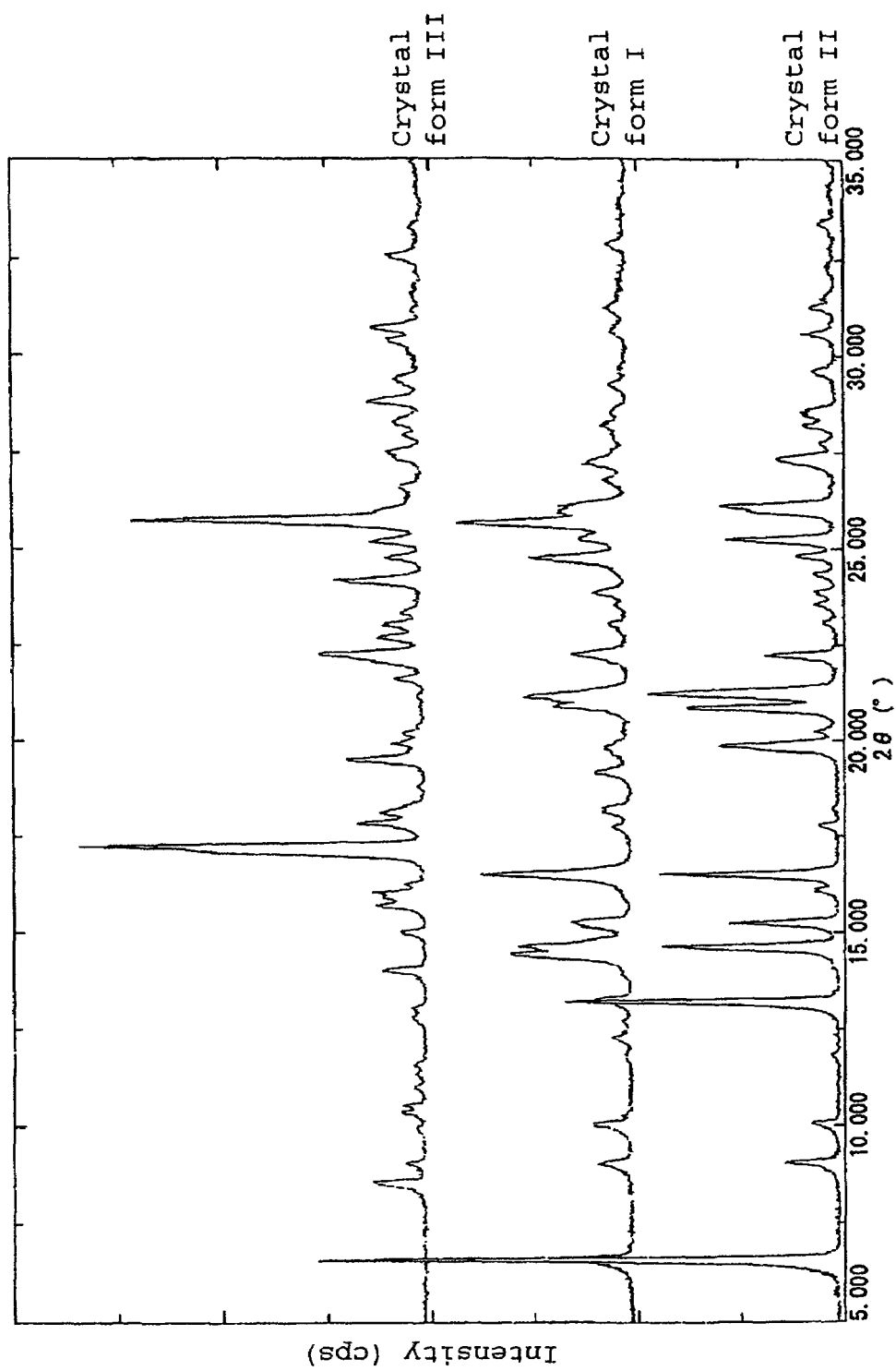
FIG. 1 shows multiple records of X-ray powder diffraction patterns, wherein the upper line shows the diffraction pattern of crystal form III, the middle line shows the diffraction pattern of crystal form I, the lower line shows the diffraction pattern of crystal form II, the vertical axis shows diffraction intensity (cps: counts per second: intervals of scale is 2500 cps) and the transverse axis shows diffraction angle 2θ(°).
Figure 2:
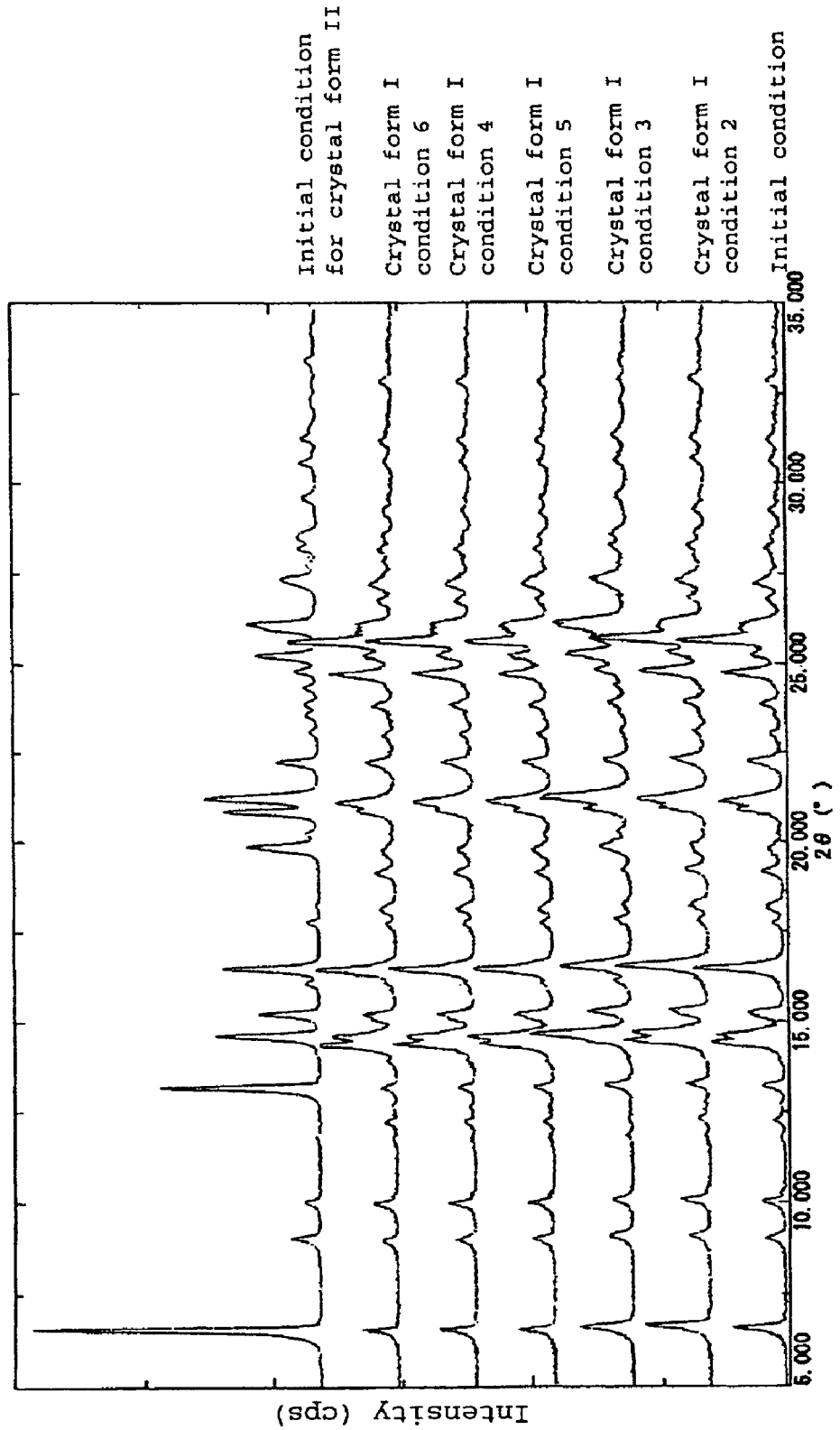
FIG. 2 shows multiple records of X-ray powder diffraction pattern obtained from the sample after 3-day preservation of the stability test of crystal form I. For comparison, the uppermost line shows the diffraction pattern (initial conditions) of crystal form II, and the lowermost line shows the diffraction pattern (initial conditions) of crystal form I. Shown from the second line are diffraction patterns under preservation condition# 6 (60° C./75% R.H., open container, 3 weeks preservation), preservation condition# 4 (60° C., container with stopper, 3 weeks preservation), preservation condition# 5 (60° C., open container, 3 weeks preservation), preservation condition# 3 (80° C., open container, 3 days preservation) and preservation condition# 2 (80° C., container with stopper, 3 days preservation) The vertical axis shows diffraction intensity (cps: counts per second: intervals of scale is 2500 cps) and the transverse axis shows diffraction angle 2θ(°).

SEQ ID; No 1: Donor + chain for determining HIV integrase activity

SEQ ID; No 2: Donor − chain for determining HIV integrase activity

SEQ ID; No 3: Target + chain for determining HIV integrase activity

SEQ ID; No 4: Target − chain for determining HIV integrase activity

The instant application includes a Statement Accompanying Sequence Listing, and a Sequence Listing in both paper and computer-readable formats.

The invention claimed is:

1. A crystal of 6-(3-chloro-2-fluorobenzyl)-1-[(S)-1-hydroxymethyl-2-methylpropyl]-7-methoxy-4-oxo-1,4-dihydroquinoline-3-carboxylic acid, having an X-ray powder diffraction pattern having characteristic diffraction peaks at diffraction angles 2θ of 6.56°, 13.20°, 19.86°, 20.84°, 21.22°, 25.22° as measured by X-ray powder diffractometer.

2. A crystal of 6-(3-chloro-2-fluorobenzyl)-1-[(S)-1-hydroxymethyl-2-methylpropyl]-7-methoxy-4-oxo-1,4-dihydroquinoline-3-carboxylic acid, having an X-ray powder diffraction pattern having characteristic diffraction peaks at diffraction angles 2θ of 8.54°, 14.02°, 15.68°, 17.06°, 17.24°, 24.16°, 25.74° as measured by X-ray powder diffractometer.

3. A crystal of 6-(3-chloro-2-fluorobenzyl)-1-[(S)-1-hydroxymethyl-2-methylpropyl]-7-methoxy-4-oxo-1,4-dihydroquinoline-3-carboxylic acid, having an extrapolated onset temperature of 162.1±5.0° C.

4. A pharmaceutical composition comprising the crystal of any one of claims 1-3, and a pharmaceutically acceptable carrier, wherein said carrier is not a liquid carrier.

5. The pharmaceutical composition of claim 4 wherein the composition is in the form of a tablet, pill, powder or granule.

6. The pharmaceutical composition of claim 5 wherein the composition is in the form of a tablet.

7. A method of inhibiting integrase comprising administering to a mammal an integrase-inhibiting amount of the crystal of any one of claims 1-3.

8. A method of treating a viral infection comprising administering to a mammal an anti-viral amount of the crystal of any one of claims 1-3.

9. A method for the treatment of an HIV infection comprising administering to an HIV-infected mammal an effective amount of the crystal of any one of claims 1-3.

10. An anti-HIV composition comprising the crystal of any one of claims 1-3 and one or more other anti-HIV active substances.

11. A method for the treatment of an HIV infection comprising administering to an HIV-infected mammal an effective amount of the crystal of any one of claims 1-3 and one or more other anti-HIV active substances.

12. The method of claim 7 wherein the mammal is a human.

13. The method of claim 8 wherein the mammal is a human.

14. The method of claim 9 wherein the mammal is a human.

15. The method of claim 11 wherein the mammal is a human.

\* \* \* \* \*

UNITED STATES PATENT AND TRADEMARK OFFICE
CERTIFICATE OF CORRECTION

| | | |
|---|---|---|
| PATENT NO. | : 7,635,704 B2 | Page 1 of 1 |
| APPLICATION NO. | : 11/133471 | |
| DATED | : December 22, 2009 | |
| INVENTOR(S) | : Satoh et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 488 days.

Delete the phrase "by 488 days" and insert -- by 237 days --

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,635,704 B2  
APPLICATION NO. : 11/133471  
DATED : December 22, 2009  
INVENTOR(S) : Satoh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 524 days.

Signed and Sealed this  
Twelfth Day of February, 2013

Teresa Stanek Rea  
*Acting Director of the United States Patent and Trademark Office*